United States Patent
Ferrari et al.

(10) Patent No.: US 7,314,612 B2
(45) Date of Patent: *Jan. 1, 2008

(54) COSMETIC COMPOSITIONS CONTAINING AT LEAST ONE HETEROPOLYMER AND AT LEAST ONE GELLING AGENT AND METHODS OF USING THE SAME

(75) Inventors: Véronique Ferrari, Maisons-Alfort (FR); Carlos O. Pinzon, New Milford, NJ (US); Paul Thau, Berkeley Heights, NJ (US)

(73) Assignee: L'Oreal S.A., Paris (FR)

( * ) Notice: Subject to any disclaimer, the term of this patent is extended or adjusted under 35 U.S.C. 154(b) by 679 days.

This patent is subject to a terminal disclaimer.

(21) Appl. No.: 10/203,254

(22) PCT Filed: Dec. 12, 2001

(86) PCT No.: PCT/IB01/02840

§ 371 (c)(1),
(2), (4) Date: Dec. 20, 2002

(87) PCT Pub. No.: WO02/058643

PCT Pub. Date: Aug. 1, 2002

(65) Prior Publication Data

US 2003/0185780 A1    Oct. 2, 2003

(30) Foreign Application Priority Data

Dec. 12, 2000    (WO) .................. PCT/IB00/02006

(51) Int. Cl.
A61K 31/74    (2006.01)
(52) U.S. Cl. ............... 424/78.08; 424/400; 424/78.02; 424/486; 424/401
(58) Field of Classification Search ............. 424/486, 424/484, 400, 78.02, 65, 78.08, 401
See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway .................. 167/85 |
| 3,141,787 A | 7/1964 | Goetze et al. |
| 3,148,125 A | 9/1964 | Strianse et al. |
| 3,156,572 A | 11/1964 | Carlick et al. |
| 3,157,681 A | 11/1964 | Fischer |
| 3,255,082 A | 6/1966 | Barton |
| 3,324,041 A | 6/1967 | Sommer et al. |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,247,411 A | 1/1981 | Vanlerberghe et al. |
| 4,275,054 A | 6/1981 | Sebag et al. |
| 4,275,055 A | 6/1981 | Nachtigal et al. ............. 424/70 |
| 4,278,658 A | 7/1981 | Hooper et al. |
| 4,279,658 A | 7/1981 | Harvey et al. |
| 4,337,298 A | 6/1982 | Karim et al. |

(Continued)

FOREIGN PATENT DOCUMENTS

CA    1319306    6/1988

(Continued)

OTHER PUBLICATIONS

Bush Boake Allen, Inc., Uniclear Formulations, dated Oct. 13, 1998.

(Continued)

*Primary Examiner*—Dameron L. Jones
(74) *Attorney, Agent, or Firm*—Finnegan, Henderson, Farabow, Garrett and Dunner, LLP

(57) ABSTRACT

The invention relates to a physiologically acceptable composition, in particular a cosmetic composition, containing at least one liquid fatty phase comprising at least one structuring polymer comprising a polymer skeleton having hydrocarbon-based repeating units containing at least one hetero atom, and and at least one gelling agent for the said fatty phase, the liquid fatty phase, the structuring polymer and the gelling agent forming a physiologically acceptable medium. This composition may be in the form of a stick of lipstick which is stable, which does not exude and whose application produces a glossy deposit with good staying power over time.

35 Claims, No Drawings

U.S. PATENT DOCUMENTS

| | | |
|---|---|---|
| 4,341,671 A | 7/1982 | Bolze et al. |
| 4,367,390 A | 1/1983 | Balleys et al. |
| 4,376,194 A | 3/1983 | Tanaka et al. |
| 4,387,090 A | 6/1983 | Bolich, Jr. ................. 424/70 |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. ............. 252/522 |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |
| 4,724,137 A | 2/1988 | Hoppe et al. |
| 4,769,285 A | 9/1988 | Rasmussen |
| 4,806,338 A | 2/1989 | Smith ......................... 424/47 |
| 4,806,345 A | 2/1989 | Bhattacharyya .............. 424/70 |
| 4,820,765 A | 4/1989 | Whyzmuzis |
| 4,822,601 A | 4/1989 | Goode et al. |
| 4,871,536 A | 10/1989 | Arraudeau et al. ........... 424/59 |
| 4,885,709 A | 12/1989 | Edgar et al. |
| 4,937,069 A | 6/1990 | Shin |
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr ............................. 424/66 |
| 5,073,364 A | 12/1991 | Giezendanner et al. |
| 5,085,859 A | 2/1992 | Halloran et al. |
| 5,102,656 A | 4/1992 | Kasat |
| 5,166,355 A | 11/1992 | Leistner et al. |
| 5,186,318 A | 2/1993 | Oestreich et al. ............. 206/37 |
| 5,196,260 A | 3/1993 | Dirschl et al. |
| 5,223,559 A | 6/1993 | Arraudeau et al. |
| 5,237,071 A | 8/1993 | Leistner et al. |
| 5,252,323 A | 10/1993 | Richard et al. |
| 5,268,029 A | 12/1993 | Demangeon et al. |
| 5,272,241 A | 12/1993 | Lucarelli et al. ............. 528/15 |
| 5,290,555 A | 3/1994 | Guthauser et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Ross et al. |
| 5,505,937 A | 4/1996 | Castrogiovanni et al. |
| 5,510,452 A | 4/1996 | Santhanam ................. 528/291 |
| 5,536,871 A | 7/1996 | Santhanam ................. 560/196 |
| 5,538,718 A | 7/1996 | Aul et al. |
| 5,538,793 A | 7/1996 | Inokuchi et al. |
| 5,540,853 A | 7/1996 | Trinh et al. ................. 510/101 |
| 5,585,091 A | 12/1996 | Pelzer et al. |
| 5,603,925 A | 2/1997 | Ross et al. .................... 424/65 |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. ............. 424/70.1 |
| 5,620,693 A | 4/1997 | Piot et al. |
| 5,645,632 A | 7/1997 | Pavlin |
| 5,667,770 A | 9/1997 | Szweda et al. ............... 424/64 |
| 5,679,357 A | 10/1997 | Dubief et al. .............. 424/401 |
| 5,683,817 A | 11/1997 | Kenmochi |
| 5,695,747 A | 12/1997 | Forestier et al. |
| 5,702,519 A | 12/1997 | Nitta et al. |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A | 7/1998 | Pavlin et al. |
| 5,795,565 A | 8/1998 | Eteve et al. |
| 5,800,816 A | 9/1998 | Brieva et al. ................. 424/63 |
| 5,807,968 A | 9/1998 | Heinrich et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,849,909 A | 12/1998 | Richard et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. ............. 424/65 |
| 5,882,363 A | 3/1999 | Spaulding et al. |
| 5,891,424 A | 4/1999 | Bretzler et al. |
| 5,897,869 A | 4/1999 | Roulier et al. .............. 424/401 |
| 5,902,592 A | 5/1999 | Bara et al. |
| 5,908,631 A | 6/1999 | Arnaud et al. |
| 5,911,974 A | 6/1999 | Brieva et al. ................. 424/64 |
| 5,919,441 A | 7/1999 | Mendolia et al. ........ 424/78.08 |
| 5,925,337 A | 7/1999 | Arraudeau et al. |
| 5,945,095 A | 8/1999 | Mougin et al. |
| 5,945,112 A | 8/1999 | Flynn et al. |
| 5,955,060 A | 9/1999 | Huglin et al. |
| 5,959,009 A | 9/1999 | Konik et al. ................. 524/261 |
| 5,961,998 A | 10/1999 | Arnaud et al. |
| 5,962,452 A | 10/1999 | Haase et al. |
| 5,965,112 A | 10/1999 | Brieva et al. ................. 424/64 |
| 5,972,095 A | 10/1999 | Graves et al. |
| 5,972,354 A | 10/1999 | de la Poterie et al. |
| 5,972,359 A | 10/1999 | Sine et al. |
| 5,976,512 A | 11/1999 | Huber |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A * | 12/1999 | Pavlin et al. ................ 528/310 |
| 6,001,980 A | 12/1999 | Borzo et al. |
| 6,004,567 A | 12/1999 | Marchi-Lemann et al. |
| 6,007,796 A | 12/1999 | Manzel et al. |
| 6,007,799 A | 12/1999 | Lee et al. |
| 6,019,962 A | 2/2000 | Rabe et al. |
| 6,036,947 A | 3/2000 | Barone et al. |
| 6,045,782 A | 4/2000 | Krog et al. |
| 6,045,823 A | 4/2000 | Vollhardt et al. |
| 6,051,216 A | 4/2000 | Barr et al. ................. 424/78.35 |
| 6,054,517 A | 4/2000 | Spaulding et al. |
| 6,060,072 A | 5/2000 | Konik et al. ................ 424/401 |
| 6,063,398 A | 5/2000 | Gueret |
| 6,066,328 A | 5/2000 | Ribier et al. |
| 6,074,654 A | 6/2000 | Drechsler et al. ........... 424/401 |
| 6,093,385 A | 7/2000 | Habeck et al. |
| 6,103,249 A | 8/2000 | Roulier et al. .............. 424/401 |
| 6,106,820 A | 8/2000 | Morrissey et al. |
| 6,111,055 A | 8/2000 | Berger et al. |
| 6,132,745 A | 10/2000 | Marchi-lemann et al. |
| 6,156,325 A | 12/2000 | Farer et al. ................. 424/401 |
| 6,156,804 A | 12/2000 | Chevalier et al. |
| 6,159,455 A | 12/2000 | Habeck et al. |
| 6,165,454 A | 12/2000 | Patel et al. |
| 6,165,971 A | 12/2000 | Oppenlander et al. |
| 6,171,347 B1 | 1/2001 | Kunz |
| 6,177,523 B1 | 1/2001 | Reich et al. ................ 525/459 |
| 6,180,117 B1 | 1/2001 | Berthiaume et al. |
| 6,180,123 B1 | 1/2001 | Mondet |

| | | | | | |
|---|---|---|---|---|---|
| 6,190,673 B1 | 2/2001 | Guskey et al. ............... 424/401 | 2002/0141958 A1 | 10/2002 | Maio et al. |
| 6,197,100 B1 | 3/2001 | Melbouci | 2002/0150602 A1 | 10/2002 | Livoreil et al. |
| 6,203,780 B1 | 3/2001 | Arnaud et al. | 2002/0159964 A1 | 10/2002 | Nakanishi et al. |
| 6,203,807 B1 | 3/2001 | Lemann | 2002/0168335 A1 | 11/2002 | Collin |
| 6,214,326 B1 | 4/2001 | Dupuis | 2002/0172696 A1 | 11/2002 | Ferrari |
| 6,214,329 B1 | 4/2001 | Brieva et al. | 2002/0189030 A1 | 12/2002 | Collin |
| 6,221,389 B1 | 4/2001 | Cannell et al. | 2002/0192168 A1 | 12/2002 | Blin et al. |
| 6,224,851 B1 | 5/2001 | Bara | 2003/0012764 A1 | 1/2003 | Collin |
| 6,242,509 B1 | 6/2001 | Berger et al. | 2003/0026772 A1 | 2/2003 | Jager-Lezer et al. |
| 6,251,375 B1 | 6/2001 | Bara | 2003/0044367 A1 | 3/2003 | Simon et al. |
| 6,251,409 B1 | 6/2001 | Hegyi et al. | 2003/0086883 A1 | 5/2003 | Feng et al. |
| 6,254,876 B1 | 7/2001 | de la Poterie et al. | 2003/0129211 A9 | 7/2003 | Livoreil |
| 6,254,877 B1 | 7/2001 | de la Poterie et al. | 2003/0147837 A1 | 8/2003 | Cavazzuti et al. |
| 6,258,345 B1 * | 7/2001 | Rouquet et al. ............... 424/64 | 2003/0161807 A1 | 8/2003 | Lemann |
| 6,264,933 B1 | 7/2001 | Bodelin et al. | 2003/0161848 A1 | 8/2003 | Ferrari et al. |
| 6,268,466 B1 | 7/2001 | MacQueen et al. | 2003/0185780 A1 | 10/2003 | Ferrari et al. |
| 6,280,846 B1 | 8/2001 | Darby et al. | 2003/0198613 A1 | 10/2003 | Feng et al. |
| 6,287,552 B1 | 9/2001 | Tournilhac et al. | 2004/0013625 A1 | 1/2004 | Kanji |
| 6,325,994 B1 | 12/2001 | Collin et al. | 2004/0028636 A1 | 2/2004 | Collin |
| 6,348,563 B1 | 2/2002 | Fukuda et al. | 2004/0042980 A1 | 3/2004 | Kanji et al. |
| 6,361,764 B2 | 3/2002 | Richard et al. | 2004/0086478 A1 | 5/2004 | Ferrari |
| 6,372,235 B1 | 4/2002 | Livoreil et al. | 2004/0091510 A1 | 5/2004 | Feng et al. |
| 6,376,078 B1 | 4/2002 | Inokuchi | 2004/0126401 A1 | 7/2004 | Collin |
| 6,383,502 B1 | 5/2002 | Dunshee et al. | 2004/0166076 A1 | 8/2004 | Ferrari et al. |
| 6,399,080 B1 | 6/2002 | Bara | 2004/0166133 A1 | 8/2004 | Cavazzuti et al. |
| 6,399,081 B1 | 6/2002 | Nakanishi et al. | 2004/0247549 A1 | 12/2004 | Lu et al. |
| 6,402,408 B1 * | 6/2002 | Ferrari ........................ 401/64 | 2005/0008598 A1 | 1/2005 | Lu et al. |
| 6,410,003 B1 | 6/2002 | Bhatia et al. | 2005/0008599 A1 | 1/2005 | Lu et al. |
| 6,423,306 B2 | 7/2002 | Caes et al. | 2005/0065261 A1 | 3/2005 | Darlington, Jr. et al. |
| 6,423,324 B1 | 7/2002 | Murphy et al. | 2005/0089491 A1 | 4/2005 | Collin |
| 6,428,773 B1 | 8/2002 | Oko et al. | 2005/0089505 A1 | 4/2005 | Collin |
| 6,432,391 B1 * | 8/2002 | Bara ........................ 424/65 | 2005/0089541 A1 | 4/2005 | Lacoutiere |
| 6,447,759 B2 | 9/2002 | Noguchi et al. | 2005/0191327 A1 | 9/2005 | Yu et al. |
| 6,469,131 B2 | 10/2002 | Lawson et al. | | | |
| 6,475,500 B2 | 11/2002 | Vatter et al. | | | |
| 6,479,686 B2 | 11/2002 | Nakanishi et al. | | | |
| 6,482,400 B1 | 11/2002 | Collin | | | |
| 6,491,931 B1 | 12/2002 | Collin | | | |
| 6,497,861 B1 | 12/2002 | Wang et al. | | | |
| 6,503,522 B2 | 1/2003 | Lawson et al. | | | |
| 6,506,716 B1 | 1/2003 | Delplancke et al. | | | |
| 6,545,174 B2 | 4/2003 | Habeck et al. | | | |
| 6,552,160 B2 | 4/2003 | Pavlin | | | |
| 6,649,173 B2 | 11/2003 | Arnaud et al. | | | |
| 6,682,748 B1 | 1/2004 | De La Poterie et al. | | | |
| 6,716,420 B2 | 4/2004 | Feng et al. | | | |
| 6,726,917 B2 | 4/2004 | Kanji et al. | | | |
| 6,749,173 B2 | 6/2004 | Heiling | | | |
| 6,761,881 B2 | 7/2004 | Bara | | | |
| 6,830,610 B1 | 12/2004 | Bruchert et al. | | | |
| 6,869,594 B2 | 3/2005 | Ferrari | | | |
| 6,875,245 B2 | 4/2005 | Pavlin | | | |
| 6,881,400 B2 | 4/2005 | Collin | | | |
| 6,960,339 B1 | 11/2005 | Ferrari | | | |
| 6,979,469 B2 | 12/2005 | Ferrari et al. | | | |

FOREIGN PATENT DOCUMENTS

| | | |
|---|---|---|
| CA | 2003346 | 5/1990 |
| DE | 38 39 136 A1 | 5/1990 |
| DE | 38 43 892 A1 | 6/1990 |
| DE | 42 08 297 A1 | 9/1993 |
| DE | 42 34 886 A1 | 4/1994 |
| DE | 195 43 988 A1 | 5/1997 |
| DE | 197 07 309 A1 | 8/1998 |
| DE | 197 26 184 A1 | 12/1998 |
| DE | 197 50 246 A1 | 5/1999 |
| DE | 197 55 649 A1 | 6/1999 |
| DE | 198 55 649 A1 | 6/2000 |
| DE | 199 51 010 A1 | 4/2001 |
| EP | 0 169 997 B1 | 2/1986 |
| EP | 0 295 886 | 12/1988 |
| EP | 0 370 470 B1 | 5/1990 |
| EP | 0 374 332 A1 | 6/1990 |
| EP | 0 412 710 B1 | 2/1991 |
| EP | 0 444 633 A2 | 9/1991 |
| EP | 0 507 692 A1 | 10/1992 |
| EP | 0 517 104 B1 | 12/1992 |
| EP | 0 518 772 A1 | 12/1992 |
| EP | 0 518 773 A1 | 12/1992 |
| EP | 0 557 196 A1 | 8/1993 |
| EP | 0 570 838 B1 | 11/1993 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |
| EP | 0 669 323 A1 | 8/1995 |
| EP | 0 673 642 B1 | 9/1995 |
| EP | 0 708 114 A1 | 4/1996 |
| EP | 0 749 746 A1 | 12/1996 |
| EP | 0 749 747 A1 | 12/1996 |
| EP | 0 749 748 A1 | 12/1996 |
| EP | 0 775 483 A1 | 5/1997 |
| EP | 0 775 698 A1 | 5/1997 |
| EP | 0 790 243 A1 | 8/1997 |

2001/0014312 A1 8/2001 Nakanishi et al.
2001/0014313 A1 8/2001 Roulier et al.
2001/0028887 A1 10/2001 Douin et al.
2001/0031280 A1 10/2001 Ferrari et al.
2001/0033846 A1 10/2001 Roulier et al.
2002/0010179 A1 1/2002 Richard et al.
2002/0044918 A1 4/2002 Bara
2002/0058053 A1 5/2002 Nakanishi et al.
2002/0081323 A1 6/2002 Nakanishi et al.
2002/0102225 A1 8/2002 Hess et al.
2002/0107314 A1 8/2002 Pinzon et al.
2002/0111330 A1 8/2002 Pinzon et al.
2002/0114771 A1 8/2002 Nakanishi
2002/0114773 A1 8/2002 Kanji et al.
2002/0119171 A1 8/2002 Gruning et al.
2002/0120036 A1 8/2002 Pinzon et al.
2002/0122781 A1 9/2002 Pinzon et al.
2002/0131947 A1 9/2002 Nakanishi

| | | | | | | |
|---|---|---|---|---|---|---|
| EP | 0 796 851 A1 | 9/1997 | | GB | 1 117 129 | 6/1968 |
| EP | 0 797 976 A2 | 10/1997 | | GB | 1 194 901 | 6/1970 |
| EP | 0 820 764 | 1/1998 | | GB | 1 194 902 | 6/1970 |
| EP | 0 847 752 A1 | 6/1998 | | GB | 1 220 069 | 1/1971 |
| EP | 0 863 145 A2 | 9/1998 | | GB | 1 273 004 | 5/1972 |
| EP | 0 877 063 B1 | 11/1998 | | GB | 1 444 204 | 7/1976 |
| EP | 0 878 469 A1 | 11/1998 | | GB | 1 539 625 | 1/1979 |
| EP | 0 879 592 A2 | 11/1998 | | GB | 2 014 852 A | 9/1979 |
| EP | 0 887 073 A1 | 12/1998 | | GB | 2 021 411 A | 12/1979 |
| EP | 0 893 119 B1 | 1/1999 | | GB | 2 147 305 A | 5/1985 |
| EP | 0 923 928 | 6/1999 | | GB | 2 196 978 A | 5/1988 |
| EP | 0 925 780 | 6/1999 | | JP | 45-41318 | 12/1970 |
| EP | 0 928 608 A2 | 7/1999 | | JP | 48-38861 | 11/1973 |
| EP | 0 930 058 B1 | 7/1999 | | JP | 49-75740 | 7/1974 |
| EP | 0 930 060 A1 | 7/1999 | | JP | 50/58242 | 5/1975 |
| EP | 0 933 376 A2 | 8/1999 | | JP | 52-007067 | 2/1977 |
| EP | 0 943 340 A1 | 9/1999 | | JP | 53/043577 | 4/1978 |
| EP | 0 958 804 A2 | 11/1999 | | JP | 56/123909 | 9/1981 |
| EP | 0 958 805 A2 | 11/1999 | | JP | 56/166276 | 12/1981 |
| EP | 0 958 811 A1 | 11/1999 | | JP | 61/065809 | 4/1986 |
| EP | 0 959 066 A2 | 11/1999 | | JP | 62061911 | 3/1987 |
| EP | 0 959 091 A1 | 11/1999 | | JP | 64-90110 | 4/1989 |
| EP | 0 967 200 A1 | 12/1999 | | JP | 2/127568 | 5/1990 |
| EP | 0 976 390 A1 | 2/2000 | | JP | 02/200612 | 8/1990 |
| EP | 0 984 025 A2 | 3/2000 | | JP | 02/207014 | 8/1990 |
| EP | 1 002 514 A1 | 5/2000 | | JP | 2/216279 | 8/1990 |
| EP | 1 018 332 | 7/2000 | | JP | 3/014683 | 1/1991 |
| EP | 1 031 342 A1 | 8/2000 | | JP | 04/346909 | 12/1992 |
| EP | 1 044 676 A2 | 10/2000 | | JP | 7/179795 | 7/1995 |
| EP | 1 048 282 A1 | 11/2000 | | JP | 7/267827 | 10/1995 |
| EP | 1 053 742 A1 | 11/2000 | | JP | 8/225316 | 9/1996 |
| EP | 1 062 944 A1 | 12/2000 | | JP | 9/20631 | 1/1997 |
| EP | 1 062 959 A1 | 12/2000 | | JP | 09/255560 | 9/1997 |
| EP | 1 064 919 A1 | 1/2001 | | JP | 09/263516 | 10/1997 |
| EP | 1 064 920 A1 | 1/2001 | | JP | 9/295922 | 11/1997 |
| EP | 1 066 814 A1 | 1/2001 | | JP | 10/001444 | 1/1998 |
| EP | 1 068 854 A1 | 1/2001 | | JP | 10/007527 | 1/1998 |
| EP | 1 068 855 A1 | 1/2001 | | JP | 10/120903 | 5/1998 |
| EP | 1 068 856 A1 | 1/2001 | | JP | 10/212213 | 8/1998 |
| EP | 1 086 945 A1 | 3/2001 | | JP | 10/259344 | 9/1998 |
| EP | 1 090 627 B1 | 4/2001 | | JP | 11/106216 | 4/1999 |
| EP | 1 095 959 A2 | 5/2001 | | JP | 11/335228 | 12/1999 |
| EP | 1 114 636 A1 | 7/2001 | | JP | 11/335242 | 12/1999 |
| EP | 1 213 011 A1 | 6/2002 | | JP | 11/335254 | 12/1999 |
| EP | 1 213 316 A2 | 6/2002 | | JP | 2000038314 A | 2/2000 |
| FR | 1 529 329 | 5/1968 | | JP | 2000038316 A | 2/2000 |
| FR | 2 232 303 | 1/1975 | | JP | 2000038317 A | 2/2000 |
| FR | 2 315 991 | 1/1977 | | JP | 2000038321 A | 2/2000 |
| FR | 2 416 008 | 8/1979 | | JP | 2000/503305 | 3/2000 |
| FR | 2 674 126 | 9/1992 | | JP | 2000086427 A | 3/2000 |
| FR | 2 785 179 | 5/2000 | | JP | 2000086429 A | 3/2000 |
| FR | 2 796 270 | 1/2001 | | JP | 2000086438 A | 3/2000 |
| FR | 2 796 271 | 1/2001 | | JP | 2000/0154112 | 6/2000 |
| FR | 2 796 272 | 1/2001 | | JP | 2002/539220 | 11/2002 |
| FR | 2 796 273 | 1/2001 | | WO | WO 86/04916 | 8/1986 |
| FR | 2 796 276 | 1/2001 | | WO | WO 87/03783 | 7/1987 |
| FR | 2 796 550 | 1/2001 | | WO | WO 91/12793 | 9/1991 |
| FR | 2 802 806 | 6/2001 | | WO | WO 93/04665 | 3/1993 |
| FR | 2 804 014 | 7/2001 | | WO | WO 93/21763 | 11/1993 |
| FR | 2 804 017 | 7/2001 | | WO | WO 93/23008 | 11/1993 |
| FR | 2 804 018 | 7/2001 | | WO | WO 94/18261 | 8/1994 |
| FR | 2 804 286 | 8/2001 | | WO | WO 94/21233 | 9/1994 |
| FR | 2 810 562 | 12/2001 | | WO | WO 95/15741 | 6/1995 |
| FR | 2 811 225 | 1/2002 | | WO | WO 95/24887 | 9/1995 |
| FR | 2 811 552 A1 | 1/2002 | | WO | WO 95/33000 | 12/1995 |
| FR | 2 816 506 | 5/2002 | | WO | WO 96/15761 | 5/1996 |
| FR | 2 817 739 | 6/2002 | | WO | WO 96/40044 | 12/1996 |
| FR | 2 817 740 | 6/2002 | | WO | WO 97/17057 | 5/1997 |
| FR | 2 817 742 | 6/2002 | | WO | WO 97/36573 | 10/1997 |
| FR | 2 817 743 | 6/2002 | | WO | WO 98/17243 | 4/1998 |
| FR | 2 819 399 | 7/2002 | | WO | WO 98/17705 | 4/1998 |
| FR | 2 819 400 | 7/2002 | | WO | WO 98/22078 | 5/1998 |
| FR | 2 819 402 | 7/2002 | | WO | WO 98/25922 | 6/1998 |

| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 00/27350 | 5/2000 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 | 7/2001 |
| WO | WO 01/52799 A1 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47606 A2 | 6/2002 |
| WO | WO 02/47608 A2 | 6/2002 |
| WO | WO 02/47619 A2 | 6/2002 |
| WO | WO 02/47620 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/47658 | 6/2002 |
| WO | WO 02/49583 A1 | 6/2002 |
| WO | WO 02/49601 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |
| WO | WO 2005/013887 A2 | 2/2005 |

OTHER PUBLICATIONS

Certified English translation of FR 1 529 329, May 1968.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104-117.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
English language DERWENT abstract of JP 2/216279.
English language DERWENT abstract of JP 3/014683.
English language DERWENT abstract of JP 7/179795.
English language DERWENT abstract of JP 7/267827.
English language abstract of JP 8/225316 from Patent Abstracts of Japan.
English language DERWENT abstract of JP 9/20631.
English language DERWENT abstract of EP 0 775 698 A1.
English language DERWENT abstract of EP 0 790 243 A1.
English language DERWENT abstract of EP 0 863 145 A2.
English language DERWENT abstract of EP 0 878 469 A1.
English language DERWENT abstract of EP 0 967 200 A1.
English language DERWENT abstranct of FR 2 315 991.
English language DERWENT abstract of FR 2 416 008.
English language DERWENT abstract of FR 2 796 550.
English language abstract of JP 78 043577.
English language DERWENT abstract of WO 01/97773.
English language DERWENT abstract of WO 02/056847.
English language DERWENT abstract of WO 02/056848.
English language DERWENT abstract of WO 02/47622.
English language DERWENT abstract of WO 02/47629.
English language DERWENT abstract of WO 02/47630.
English language DERWENT abstract of WO 86/04916.
English language DERWENT abstract of WO 93/04665.
English language DERWENT abstract of WO 98/25922.
Estee Lauder's Amended Answer and Counterclaims, dated Apr. 21, 2005, in the on-going litigation *L'Oreal S.A., et al., v. The Estee Lauder Companies Inc., et al.*, Civil Action No. 04-1660 (D.N.J.).
Estee Lauder's Response to Plaintiff's First Set of Interrogatories (Nos. 1-6), dated Sep. 27, 2004, in the on-going litigation *L'Oreal S.A., et al. v. The Estee Lauder Companies Inc., et al.*, Civil Action No. 04-1660 (D.N.J.).
Estee Lauder's Response to Plaintiff's Third Set of Interrogatories (Nos. 8-13), dated Jun. 21, 2005, in the on-going litigation *L'Oreal S.A., et al. v. The Estee Lauder Companies Inc., et al.*, Civil Action No. 04-1660 (D.N.J.).
International Search Report in PCT/US03/41618, dated Mar. 11, 2005.
International Search Report in PCT/US04/01071, dated Feb. 22, 2005.
Co-Pending U.S. Appl. No. 10/450,108, Title: Cosmetic Composition Comprising a Polymer and Fibres, filed Jun. 11, 2003.
Co-Pending U.S. Appl. No. 10/459,636, Title: Cosmetic Emulsions Containing at Least One Hetero Polymer and at Least One Sunscreen and Methods of Using the Same, filed Jun. 12, 2003.
Co-Pending U.S. Appl. No. 10/466,166, Title: Cosmetic Composition Comprising a Mixture of Polymers, filed Jul. 14, 2003.
Co-Pending U.S. Appl. No. 10/618,315, Title: Cosmetic Compositions Comprising a Structuring Agent, Silicone Powder and Swelling Agent, filed Jul. 11, 2003.
Co-Pending U.S. Appl. No. 10/699,780, Title: Methods of Dispersing at Least One Coloring Agent Using at Least one Heteropolymer, filed Nov. 4, 2003.
Co-Pending U.S. Appl. No. 10/746,612, Title: Cosmetic Compositions Comprising a Structuring Agent, Silicone Powder and Swelling Agent, filed Dec. 22, 2003.
Co-Pending U.S. Appl. No. 10/747,412, Title: Cosmetic Emulsions Containing at Least One Hetero Polymer and at Least One Sunscreen and Methods of Using the Same, filed Dec. 22, 2003.
Co-Pending U.S. Appl. No. 10/787,440, Title: Compostition Comprising at Least one Hetero Polymer and at Least one Inert Filler and Methods for Use, filed Feb. 27, 2004.
Co-Pending U.S. Appl. No. 10/787,441, Title: Cosmetic Composition Comprising Hetero Polymers and a Solid Substance and Method of Using Same, filed Feb. 27, 2004.
Co-Pending Application No. Not Yet Assigned; Title: Compositions Containing Heteropolymers and Oilsoluble Esters and Methods of Using Same, U.S. Filing Date: Aug. 16, 2004.
English language abstract of JP 53043577 from Patent Abstracts of Japan.
English language abstract of JP 56123909 from Patent Abstracts of Japan.
English language abstract of JP 56166276 from Patent Abstracts of Japan.
English language DERWENT abstract of JP 61065809.
English language DERWENT abstract of DE 195 43 988 A1.
English language DERWENT abstract of DE 197 07 309 A1.
English language DERWENT abstract of DE 197 50 246 A1.
English language DERWENT abstract of DE 199 51 010 A1.
English Language DERWENT abstract of DE 38 39 136 A.
English language DERWENT abstract of DE 38 43 892 A.
English language DERWENT abstract of DE 42 08 297 A1.
English language DERWENT abstract of DE 42 34 886 A1.
English language DERWENT abstract of EP 0 169 997 B1.
English language DERWENT abstract of EP 0 557 196 A1.
English language DERWENT abstract of EP 0 609 132 B1.
English language DERWENT abstract of EP 0 749 746 A1.
English language DERWENT abstract of EP 0 749 747 A1.
English language DERWENT abstract of EP 0 749 748 A1.
English language DERWENT abstract of EP 0 775 483 A1.
English language DERWENT abstract of EP 0 847 752 A1.
English language DERWENT abstract of EP 0 879 592 A2.

English language DERWENT abstract of EP 0 887 073 A1.
English language DERWENT abstract of EP 0 930 058 B1.
English language DERWENT abstract of EP 0 930 060 A1.
English language DERWENT abstract of EP 0 958 811 A1.
English language DERWENT abstract of EP 0 959 066 A2.
English language DERWENT abstract of EP 0 959 091 A1.
English language DERWENT abstract of EP 0 976 390 A1.
English language DERWENT abstract of EP 0 984 025 A2.
English language DERWENT abstract of EP 1 002 514 A1.
English language DERWENT abstract of EP 1 031 342 A1.
English language DERWENT abstract of EP 1 048 282 A1.
English language DERWENT abstract of EP 1 053 742 A1.
English language DERWENT abstract of EP 1 064 919 A1.
English language DERWENT abstract of EP 1 064 920 A1.
English language DERWENT abstract of EP 1 066 814 A1.
English language DERWENT abstract of EP 1 068 854 A1.
English language DERWENT abstract of EP 1 068 855 A1.
English language DERWENT abstract of EP 1 086 945 A1.
English language DERWENT abstract of EP 1 090 627 B1.
English language DERWENT abstract of EP 1 114 636 A1.
English language DERWENT abstract of FR 2 232 303.
English language DERWENT abstract of FR 2 674 126.
English language DERWENT abstract of FR 2 785 179.
English language DERWENT abstract of FR 2 796 272.
English language DERWENT abstract of FR 2 796 273.
English language DERWENT abstract of FR 2 802 806.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of FR 2 819 402.
English language DERWENT abstract of JP 04/346909.
English language DERWENT abstract of JP 10/120903.
English language DERWENT abstract of JP 10/259344.
English language DERWENT abstract of JP 11/106216.
English language DERWENT abstract of JP 11/335228.
English language DERWENT abstract of JP 11/335242.
English language DERWENT abstract of JP 11/335254.
English language DERWENT abstract of JP 2/127568.
English language DERWENT abstract of JP 2000038314 A.
French Search Report in FR 0000920 (priority document for PCT/FR01/00229), dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
French Search Report in FR 0016163, dated Aug. 1, 2001.
French Search Report in FR 0016164, dated Sep. 6, 2001.
Bangham, A.D. et al. Diffusion of Univalent Ions across the Lamellae of Swollen Phospholipids, Journal of Molecular Biology, pp. 238-252, Vol. 13, Aug. to Oct. 1965.
Co-Pending U.S. Appl. No. 10/494,864; Title: Composition Containing an Amino Acid N-Acylated Ester and a Polyamide-Structured UV Filter, filed Nov. 23, 2004.
Co-Pending U.S. Appl. No. 10/990,475, Title: Use of a Polymer for Obtaining an Express Make-Up of Keratin Materials, filed Nov. 18, 2004.
Co-Pending U.S. Appl. No. 10/993,430, Title: Cosmetic Composition Comprising a Polymer Blend, filed Nov. 22, 2004.
Co-Pending U.S. Appl. No. 10/993,431, Title: a Transfer-Free Composition Structured in Rigid Form by a Polymer, filed Nov. 22, 2004.
Co-Pending U.S. Appl. No. 11/019,382, Title: Cosmetic Composition Comprising Two Different Hetero Polymers and Method of Using Same, filed Dec. 23, 2004.
English language DERWENT abstract of DE 197 26 184, date not available.
English language DERWENT abstract of DE 197 55 649 A1, date not available.
English language DERWENT abstract of DE 198 55 649 A1, date not available.
English language DERWENT abstract of EP 0 507 692 A1, date not available.
English language DERWENT abstract of EP 0 518 772 A1, date not available.
English language DERWENT abstract of EP 0 518 773 A1, date not available.
English language DERWENT abstract of EP 0 669 323 A1, date not available.
English language DERWENT abstract of EP 0 775 698 A1, date not available.
English language DERWENT abstract of EP 0 790 243 A1, date not available.
English language DERWENT abstract of EP 0 863 145 A2, date not available.
English language DERWENT abstract of EP 0 878 469 A1, date not available.
English language DERWENT abstract of EP 0 967 200 A1, date not available.
English language DERWENT abstract of FR 2 315 991, date not available.
English language DERWENT abstract of FR 2 416 008, date not available.
English language DERWENT abstract of FR 2 796 550, date not available.
English language abstract of JP 78 043577, date not available.
English language DERWENT abstract of WO 01/97773, date not available.
English language DERWENT abstract of WO 02/056847, date not available.
English language DERWENT abstract of WO 02/056848, date not available.
English language DERWENT abstract of WO 02/47622, date not available.
English language DERWENT abstract of WO 02/47629, date not available.
English language DERWENT abstract of WO 02/47630, date not available.
English language DERWENT abstract of WO 86/04916, date not available.
English language DERWENT abstract of WO 93/04665, date not available.
English language DERWENT abstract of WO 98/25922, date not available.
McCutcheon's vol. 1: Emulsifiers & Detergents, North American Edition MC Publishing Co., Glen Rock NJ (1993), pp. 272-273.
Richard J. Lewis, Sr., "Ricinoleic Acid," Hawley's Condensed Chemical Dictionary 272 (13th. 1997).
U.S. District Court for the District of New Jersey Civil Docket for L'Oreal S.A. et al. v. Estee Lauder Companies, Inc., et al., Civ. No. 04-1660 (HAA) (filed Apr. 7, 2004) (retrieved Jan. 2, 2005).
English Language Abstract of FR 2 804 014 from esp@cenet.
English Language Abstract of FR 2 817 742 from esp@cenet.
Harry's Cosmeticology 375-383 (J.B. Wilkinson & R.J. Moore eds., Chemical Pub. 7th ed. 1982).
Patent Abstracts of Japan of 2/207014.
Co-Pending U.S. Appl. No. 11/212,811, Title: A Transfer-Free Mascara Composition Comprising at Least One Volatile Solvent and at Least One Polymer, filed Aug. 29, 2005.
Office Action in co-pending U.S. Appl. No. 10/312,083 dated Sep. 28, 2005 (Ex. Venkat).
Office Action in co-pending U.S. Appl. No. 09/749,036 dated Nov. 23, 2005 (Ex. Venkat).
Co-Pending U.S. Appl. No. 11/351,309, Title: Cosmetic Composition Containing a Polymer and a Fluoro Oil, filed Feb. 10, 2006.
Office Action in co-pending U.S. Appl. No. 09/618,066 dated Dec. 21, 2001 (Ex. Seidleck).
Office Action in co-pending U.S. Appl. No. 09/618,066 dated Jul. 15, 2002 (Ex. Sheikh).

Office Action in co-pending U.S. Appl. No. 09/618,066 dated Jul. 16, 2003 (Ex. Sheikh).
Office Action in co-pending U.S. Appl. No. 09/618,066 dated Nov. 19, 2003 (Ex. Sheikh).
Office Action in co-pending U.S. Appl. No. 09/685,577 dated Aug. 11, 2004 (Ex. Venkat).
Office Action in co-pending U.S. Appl. No. 09/685,577 dated Jul. 15, 2002 (Ex. Sheikh).
Office Action in co-pending U.S. Appl. No. 09/685,577 dated Jul. 16, 2003 (Ex. Sheikh).
Office Action in co-pending U.S. Appl. No. 09/685,577 dated Nov. 19, 2003 (Ex. Sheikh).
Office Action in co-pending U.S. Appl. No. 09/685,578 dated Aug. 11, 2004 (Ex. Pryor).
Office Action in co-pending U.S. Appl. No. 09/685,578 dated May 7, 2003 (Ex. Pryor).
Office Action in co-pending U.S. Appl. No. 09/685,578 dated Nov. 19, 2003 (Ex. Pryor).
Office Action in co-pending U.S. Appl. No. 09/685,578 dated Feb 8, 2005 (Ex. Pryor).
Office Action in co-pending U.S. Appl. No. 09/733,896 dated Jan. 28, 2003 (Ex. Rajguru).
Office Action in co-pending U.S. Appl. No. 09/733,896 dated Jul. 19, 2002 (Ex. Rajguru).
Office Action in co-pending U.S. Appl. No. 09/733,896 dated Nov. 18, 2003 (Ex. Rajguru).
Office Action in co-pending U.S. Appl. No. 09/733,896 dated Jul. 13, 2005 (Ex. Nutter).
Office Action in co-pending U.S. Appl. No. 09/733,896 dated Jan. 30, 2006 (Ex. Nutter).
Office Action in co-pending U.S. Appl. No. 09/733,897 dated Apr. 15, 2002 (Ex. Berman).
Office Action in co-pending U.S. Appl. No. 09/733,897 dated Apr. 23, 2003 (Ex. Wells).
Office Action in co-pending U.S. Appl. No. 09/733,897 dated Aug. 29, 2002 (Ex. Berman).
Office Action in co-pending U.S. Appl. No. 09/733,897 dated May 6, 2004 (Ex. Yu).
Office Action in co-pending U.S. Appl. No. 09/733,897 dated Feb. 8, 2006 (Ex. Venkat).
Office Action in co-pending U.S. Appl. No. 09/733,898 dated Apr. 29, 2003 (Ex. Yoon).
Office Action in co-pending U.S. Appl. No. 09/733,898 dated Aug. 28, 2002 (Ex. Yoon).
Office Action in co-pending U.S. Appl. No. 09/733,898 dated Dec. 23, 2003 (Ex. Yoon).
Office Action in co-pending U.S. Appl. No. 09/733,898 dated Apr. 25, 2005 (Ex. Yoon).
Office Action in co-pending U.S. Appl. No. 09/733,899 dated Sep. 22, 2004 (Ex. Venkat).
Office Action in co-pending U.S. Appl. No. 09/733,899 dated Apr. 7, 2004 (Ex. Lamm).
Office Action in co-pending U.S. Appl. No. 09/733,899 dated Apr. 9, 2003 (Ex. Lamm).
Office Action in co-pending U.S. Appl. No. 09/733,899 dated May 3, 2005 (Ex. Venkat).
Office Action in co-pending U.S. Appl. No. 09/733,900 dated Apr. 7, 2004 (Ex. Lamm).
Office Action in co-pending U.S. Appl. No. 09/733,900 dated Jul. 16, 2003 (Ex. Lamm).
Office Action in co-pending U.S. Appl. No. 09/733,900 dated Dec. 1, 2004 (Ex. Venkat).
Office Action in co-pending U.S. Appl. No. 09/733,900 dated Jun. 2, 2005 (Ex. Venkat).
Office Action in co-pending U.S. Appl. No. 09/749,036 dated Aug. 13, 2003 (Ex. Howard).
Office Action in co-pending U.S. Appl. No. 09/749,036 dated Jul. 16, 2002 (Ex. Howard).
Office Action in co-pending U.S. Appl. No. 09/749,036 dated May 5, 2004 (Ex. Howard).
Office Action in co-pending U.S. Appl. No. 09/749,036 dated Apr. 29, 2005 (Ex. Venkat).
Office Action in co-pending U.S. Appl. No. 09/899,909 dated Dec. 18, 2001 (Ex. Dodson).
Office Action in co-pending U.S. Appl. No. 09/937,314 dated May 19, 2004 (Ex. Venkat).
Office Action in co-pending U.S. Appl. No. 09/971,028 dated Aug. 11, 2003 (Ex. Wang).
Office Action in co-pending U.S. Appl. No. 09/971,028 dated Mar. 26, 2003 (Ex. Wang).
Office Action in co-pending U.S. Appl. No. 10/012,029 dated Nov. 20, 2002 (Ex. Venkat).
Office Action in co-pending U.S. Appl. No. 10/012,029 dated Sep. 08, 2003 (Ex. Venkat).
Office Action in co-pending U.S. Appl. No. 10/012,051 dated Jan. 14, 2003 (Ex. Venkat).
Office Action in co-pending U.S. Appl. No. 10/012,051 dated May 14, 2004 (Ex. Venkat).
Office Action in co-pending U.S. Appl. No. 10/012,051 dated Oct. 3, 2003 (Ex. Venkat).
Office Action in co-pending U.S. Appl. No. 10/012,052 dated Nov. 6, 2003 (Ex. Wells).
Office Action in co-pending U.S. Appl. No. 10/012,052 dated Aug. 9, 2004 (Ex. Wells).
Office Action in co-pending U.S. Appl. No. 10/012,052 dated Jun. 3, 2005 (Ex. Venkat).
Office Action in co-pending U.S. Appl. No. 10/046,568 dated Sep. 22, 2004 (Ex. Venkat).
Office Action in co-pending U.S. Appl. No. 10/046,568 dated Dec. 30, 2003 (Ex. Venkat).
Office Action in co-pending U.S. Appl. No. 10/046,568 dated Jun. 12, 2003 (Ex. Venkat).
Office Action in co-pending U.S. Appl. No. 10/046,568 dated Nov. 5, 2002 (Ex. Venkat).
Office Action in co-pending U.S. Appl. No. 10/047,987 dated Dec. 11, 2003 (Ex. Venkat).
Office Action in co-pending U.S. Appl. No. 10/047,987 dated Sep. 7, 2004 (Ex. Venkat).
Office Action in co-pending U.S. Appl. No. 10/129,377 dated Jan. 13, 2006 (Ex. Venkat).
Office Action in co-pending U.S. Appl. No. 10/182,830 dated Aug. 24, 2004 (Ex. Venkat).
Office Action in co-pending U.S. Appl. No. 10/182,830 dated Apr. 4, 2005 (Ex. Venkat).
Office Action in co-pending U.S. Appl. No. 10/182,830 dated Nov. 25, 2005 (Ex. Venkat).
Office Action in co-pending U.S. Appl. No. 10/198,931 dated Dec. 18, 2003 (Ex. Venkat).
Office Action in co-pending U.S. Appl. No. 10/198,931 dated Sep. 1, 2004 (Ex. Venkat).
Office Action in co-pending U.S. Appl. No. 10/203,018 dated May 19, 2004 (Ex. Venkat).
Office Action in co-pending U.S. Appl. No. 10/203,375 dated May 13, 2004 (Ex. Punnose).
Office Action in co-pending U.S. Appl. No. 10/312,083 dated Apr. 18, 2005 (Ex. Venkat).
Office Action in co-pending U.S. Appl. No. 10/312,083 dated Oct. 1, 2004 (Ex. Venkat).
Office Action in co-pending U.S. Appl. No. 10/413,217 dated Sep. 9, 2004 (Ex. Venkat).
Office Action in co-pending U.S. Appl. No. 10/699,780 dated Sep. 22, 2004 (Ex. Venkat).
Office Action in co-pending U.S. Appl. No. 10/699,780 dated Jun. 15, 2005 (Ex. Venkat).
Office Action in co-pending U.S. Appl. No. 10/746,612 dated Sep. 20, 2004 (Ex. Venkat).
Office Action in co-pending U.S. Appl. No. 10/746,612 dated Jun. 15, 2005 (Ex. Venkat).
Office Action in co-pending U.S. Appl. No. 10/787,440 dated Aug. 24, 2004 (Ex. Venkat).
Office Action in co-pending U.S. Appl. No. 10/787,441, dated Apr. 5, 2005 (Ex. Venkat).
Office Action in co-pending U.S. Appl. No. 10/990,475 dated Nov. 2, 2005 (Ex. Venkat).

Office Action in co-pending U.S. Appl. No. 11/212,811 dated Nov. 17, 2005 (Ex. Venkat).
English Language Abstract of FR 2 804 014 from esp@cenet, date not available.
English Language Abstract of FR 2 817 742 from esp@cenet, date not available.
Patent Abstracts of Japan of 2/207014, date not available.
English language DERWENT abstract of JP A 62061911, date not available.
English language DERWENT abstract of JP 02/200612, date not available.
English language DERWENT abstract of JP 09/255560, date not available.
English language DERWENT abstract of JP 10/007527, date not available.
English language DERWENT abstract of EP 0 820 764 A1, date not available.
English language DERWENT abstract of JP 10/212213, date not available.
English language DERWENT abstract of EP 0 923 928 A1, date not available.
English language DERWENT abstract of EP 0 925 780 A1, date not available.
English language DERWENT abstract of EP 0 943 340 A1, date not available.
English language DERWENT abstract of EP 1 068 856 A1, date not available.
English language DERWENT abstract of FR 2 796 270, date not available.
English language DERWENT abstract of FR 2 796 271, date not available.
English language DERWENT abstract of FR 2 796 276, date not available.
English language DERWENT abstract of FR 2 811 552 A1, date not available.
English language DERWENT abstract of FR 2 816 506, date not available.
Milan Jokić et al., *A Novel Type of Small Organic Gelators: Bis(Amino Acid) Oxalyl Amides*, 1995 J. Chem. Soc., Chem. Commun., 1723.
Kenji Hanabusa et al., *Prominent Gelation and Chiral Aggregation of Alkylamides Derived from trans-1,2-Diaminocyclohexane*, Angew. Chem. Int. Ed. Engl. 1996, 35, No. 17, 1949-1951.
Toshimi Shimizu et al., *Stereochemical Effect of Even-Odd Connecting Links on Supramolecular Assemblies Made of 1-Glucosamide Bolaamphiphiles*, J. Am Chem. Soc. 1997, 119, 2812-2818.
P. Terech, "Low-Molecular Weight Organogelators," in *Specialist Surfactants*, ch. 8, pp. 208-268 (I.D. Robb, ed., 1997).
Kenji Hanabusa et al., *Terephthaloyl Derivatives as New Gelators; Excellent Gelation Ability and Remarkable Increase of Gel Strength by Adding Polymers*, 1999 Chemistry Letters 767.
Xuzhong Luo et al., *Self-assembled organogels formed by monoalkyl derivatives of oxamide*, 2000 Chem. Commun. 2091-92.
Kenji Hanabusa et al., *Easy Preparation and Gelation of New Gelator Based on L-Lysine*, 2000 Chem. Letters, 1070.
PCT Application No. PCT/IB01/02780; Title: Cosmetic Compositions Containing at Least One Heteropolymer and at Least One Organogelator International Filing Date: Dec. 12, 2001.
Co-Pending U.S. Appl. No. 09/733,899; Title: Cosmetic Compositions Containing at Least One Hetero Polymer and at Least One Film-Forming Silicone Resin and Methods of Using Inventors: Mohamed Kanji et al., filed Dec. 12, 2000.
Co-Pending U.S. Appl. No. 09/733,900; Title: Cosmetic Compositions Containing Heteropolymers and Oil-Soluble Cationic Surfactants and Methods of Using Inventors: Carlos Pinzon and Paul Thau, filed Dec. 12, 2000.
Co-Pending U.S. Appl. No. 09/618,066; Title: Compositions in Rigid Form Structured with a Polymer Inventors: Véronique Ferrari and Pascal Simon, filed Jul. 17, 2000.
Co-Pending U.S. Appl. No. 09/658,577; Title: Compositions in Rigid Form Structured with a Polymer Inventors: Véronique Ferrari and Pascal Simon, filed Oct. 11, 2000.
Co-Pending U.S. Appl. No. 09/685,578; Title: Composition Containing a Liquid Fatty Phase Gelled with a Polyamide Containing Ester End Groups Inventor: Véronique Ferrari, filed Jul. 17, 2000.
Co-Pending U.S. Appl. No. 09/685,578; Title: Composition Containing a Liquid Fatty Phase Gelled with a Polyamide Containing Ester End Groups Inventor: Véronique Ferrari, filed Oct. 11, 2000.
PCT Application No. PCT/US00/33596; Title Cosmetic Composition Comprising Hetero Polymers and a Solid Substance and Method of Using Same Inventors: Roberto Cavazzuti et al. International Filing Date: Dec. 12, 2000.
Co-Pending U.S. Appl. No. 09/733,896; Title: Compositions Containing Heteropolymers and Oil-Soluble Polymers and Methods of Using Same Inventors: Carlos Pinzon and Paul Thau, filed Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau, filed Dec. 12, 2000.
Co-Pending U.S. Appl. No. 09/733,897; Title: Compositions Containing Heteropolymers and Methods of Using Same Inventors: Carlos Pinzon and Paul Thau, filed Dec. 12, 2000 Amendment filed Jan. 4, 2002 (adding claims 41-102).
PCT Application No. PCT/IB00/02000; Title: Compositions Comprising at Least One Heteropolymer and at Least One Inert Filler and Methods for Use Inventors: Véronique Ferrari et al. International Filing Date: Dec. 12, 2000.
PCT Application No. PCT/IB00/02006; Title: Cosmetic Compositions Containing at Least One Heteropolymer and at Least One Gelling Agent and Methods of Using the Same Inventor: Véronique Ferrari International Filing Date: Dec. 12, 2000.
Co-Pending U.S. Appl. No. 09/749,036; Title: Composition Comprising at Least One Hetero Polymer and at Least One Pasty Fatty Substance and Methods for Use Inventors: Véronique Ferrari et al. filed Dec. 28, 2000.
PCT Application No. PCT/US01/47459; Title: Cosmetic Compositions Containing at Least One Heteropolymer and at Least One Film-Forming Silicone Resin and Methods of Using Inventors: Mohamed Kanji et al. U.S. Filing Date: Dec. 12, 2001.
PCT Application No. PCT/US01/47499; Title: Cosmetic Compositions Containing Heteropolymers and Oil-Soluble Cationic Surfactants and Methods of Using Same Inventors: Carlos Pinzon and Paul Thau U.S. Filing Date: Dec. 12, 2001.
PCT Application No. PCT/FR01/03965; Title Cosmetic Composition Comprising Hetero Polymers and a Solid Substance and Method of Using Same Inventors: Roberto Cavazzuti et al. International Filing Date: Dec. 12, 2001.
PCT Application No. PCT/US01/47454; Title: Compositions Containing Heteropolymers and Oil-Soluble Polymers and Methods of Using Same Inventors: Carlos Pinzon and Paul Thau U.S. Filing Date: Dec. 12, 2001.
PCT Application No. PCT/US01/47497; Title: Compositions Containing Heteropolymers and Oil-Soluble Esters and Methods of Using Same Inventors: Carlos Pinzon and Paul Thau U.S. Filing Date: Dec. 12, 2001.
PCT Application No. PCT/US01/47496; Title: Compositions Containing Heteropolymers and Methods of Using Same Inventors: Carlos Pinzon and Paul Thau U.S. Filing Date: Dec. 12, 2001.
PCT Application No. PCT/FR01/03962; Title: Compositions Comprising at Least One Heteropolymer and at Least One Inert Filler and Methods for Use Inventors: Véronique Ferrari et al. International Filing Date: Dec. 12, 2001.
PCT Application No. PCT/FR01/03963; Title: Cosmetic Compositions Containing at Least One Heteropolymer and at Least One Gelling Agent and Methods of Using the Same Inventor: Véronique Ferrari International Filing Date: Dec. 12, 2001.
Co-Pending Application No. 10/129,377; Title: Cosmetic Compositions Containing at Least One Heteropolymer and at Least One Organogelator filed May 3, 2002.
International Search Report in PCT/US 01/47499, dated Aug. 8, 2002.
International Search Report in PCT/US 01/47454, dated Aug. 29, 2002.

Partial International Search Report in PCT/US 01/47497, dated Aug. 30, 2002.
Co-Pending U.S. Appl. No. 11/406,371; Title: Cosmetic Composition Comprising Silica Particles, Reflecting Particles, and at Least One Polymer, Preparative Process, and Uses Thereof, filed Apr. 19, 2006.
English language Abstract from Patent Abstracts of Japan for JP 2000/0154112.
English language Derwent abstract for JP 09/263516.
English language Derwent abstract for JP 45-41318, date not available.
English language Derwent abstract for JP 48-38861, date not available.
English language Derwent abstract for JP 49-75740, date not available.
English language Derwent abstract for JP 64-90110, date not available.
English language DERWENT abstract of FR 2,804,286, date not available.
English language esp@cenet abstract for JP 10/001444, date not available.
English language esp@cenet abstract for JP 52/007067, date not available.
English language esp@cenet abstract for JP 2002/539220, date not available.
Estee Lauder's Answer and Counterclaims, dated May 27, 2004, in the on-going litigation *L'Oreal S.A., et al.,* v. *The Estee Lauder Companies Inc., et al.*, Civil Action No. 04-1660 (D.N.J.).
L'Oreal's Complaint for Patent Infringement, dated Apr. 7, 2004, in the on-going litigation *L'Oreal S.A., et al.,* v. *The Estee Lauder Companies Inc., et al.*, Civil Action No. 04-1660 (D.N.J.).
Office Action in co-pending U.S. Appl. No. 09/733,897 dated Jul. 27, 2006 (Ex. Venkat).
Office Action in co-pending U.S. Appl. No. 09/733,898 dated Jan. 11, 2006 (Ex. Yoon).
Office Action in co-pending U.S. Appl. No. 10/182,830, dated May 17, 2006 (Ex. Venkat).
Office Action in co-pending U.S. Appl. No. 10/312,083 dated Apr. 6, 2006 (Ex. Venkat).
Office Action in co-pending U.S. Appl. No. 10/746,612 dated Feb. 17, 2006 (Ex. Venkat).
Office Action in co-pending U.S. Appl. No. 10/990,475 dated May 1, 2006 (Ex. Venkat).
Richard J. Lewis, Sr., "Fatty Acid," Hawley's Condensed Chemical Dictionary 487 (13th ed., 1997).
Certified English translation of FR 1 529 329.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104-107.
Co-Pending U.S. Appl. No. 09/899,909, issued as U.S. Patent No. 6,432,391 on Aug. 13, 2002, Title: Transparent Scented Solid Cosmetic Composition, filed Jul. 9, 2001.
Co-Pending U.S. Appl. No. 09/937,314; Title: Transfer-Free Composition Structured in the Stiff Form by a Polymer filed Sep. 24, 2001.
Co-Pending U.S. Appl. No. 09/971,028, issued as U.S. Patent No. 6,716,420 on Apr. 6, 2004; Title: Methods of Dispersing at Least One Coloring Agent Using at Least One Heteropolymer, Oct. 5, 2001
Co-Pending U.S. Appl. No. 10/012,029; Title: Cosmetic Composition Comprising a Polymer Blend, filed Dec. 11, 2001.
Co-Pending U.S. Appl. No. 10/012,051; Title: Use of a Polymer for Obtaining an Express Make-up of Keratin Materials, filed Dec. 11, 2001.
Co-Pending U.S. Appl. No. 10/012,052; Title: Cosmetic Composition Comprising a Wax and a Polymer, filed Dec. 11, 2001.
Co-Pending U.S. Appl. No. 10/046,568; Title: Nail Polish Comprising a Polymer, filed Jan. 16, 2002.
Co-Pending U.S. Appl. No. 10/047,987, Title: Cosmetic Composition Containing a Polymer and a Fluoro Oil, filed Jan. 17, 2002.
Co-Pending U.S. Appl. No. 10/182,830; Title: Cosmetic Composition Comprising Hetero Polymers and a Solid Substance and Method of Using Same, filed Aug. 2, 2002.
Co-Pending U.S. Appl. No. 10/198,931, Title: Compositions Comprising at Least One Heteropolymer and Fibers, and Methods of Using the Same, filed Jul. 22, 2002.
Co-Pending U.S. Appl. No. 10/203,018; Title: Composition Comprising at Least One Hetero Polymer and at Least One Inert Filler and Methods for Use, filed Aug. 5, 2002.
Co-Pending U.S. Appl. No. 10/203,254; Title: Cosmetic Compositions Containing at Least One Heteropolymer and at Least One Gelling Agent and Methods of Using the Same, filed Aug. 7, 2002.
Co-Pending U.S. Appl. No. 10/203,374; Title: Method for Making a Coloured Make-Up Cosmetic Compositions with Controlled Transmittance, filed Aug 9, 2002.
Co-Pending U.S. Appl. No. 10/203,375, Title: Transparent or Translucent Colored Cosmetic Composition, filed Aug. 9, 2002.
Co-Pending U.S. Appl. No. 10/312,083, Title: Solid Emulsion Containing a Liquid Fatty Phase Structured with a Polymer, filed Dec. 23, 2002.
Co-Pending U.S. Appl. No. 10/413,217, Title: Methods of Dispersing at Least One Coloring Agent Using at Least One Heteropolymer, filed Apr. 15, 2003.
English language abstract of JP 53043577 from Patent Abstracts of Japan, date not available.
English language abstract of JP 56123909 from Patent Abstracts of Japan, date not available.
English language abstract of JP 56166276 from Patent Abstracts of Japan, date not available.
English language DERWENT abstract of JP 61065809, date not available.
English language DERWENT abstract of DE 195 43 988 A1, date not available.
English language DERWENT abstract of DE 197 07 309 A1, date not available.
English language DERWENT abstract of DE 197 50 246 A1, date not available.
English language DERWENT abstract of DE 199 51 010 A1, date not available.
English language DERWENT abstract of DE 38 39 136 A, date not available.
English language DERWENT abstract of DE 38 43 892 A, date not available.
English language DERWENT abstract of DE 42 08 297 A1, date not available.
English language DERWENT abstract of DE 42 34 886 A1, date not available.
English language DERWENT abstract of EP 0 169 997 B1, date not available.
English language DERWENT abstract of EP 0 557 196 A1, date not available.
English language DERWENT abstract of EP 0 609 132 B1, date not available.
English language DERWENT abstract of EP 0 749 746 A1, date not available.
English language DERWENT abstract of EP 0 749 747 A1, date not available.
English language DERWENT abstract of EP 0 749 748 A1, date not available.
English language DERWENT abstract of EP 0 775 483 A1, date not available.
English language DERWENT abstract of EP 0 847 752 A1, date not available.
English language DERWENT abstract of EP 0 879 592 A2, date not available.
English language DERWENT abstract of EP 0 887 073 A1, date not available.
English language DERWENT abstract of EP 0 930 058 B1, date not available.
English language DERWENT abstract of EP 0 930 060 A1, date not available.
English language DERWENT abstract of EP 0 958 811 A1, date not available.

English language DERWENT abstract of EP 0 959 066 A2, date not available.
English language DERWENT abstract of EP 0 959 091 A1, date not available.
English language DERWENT abstract of EP 0 976 390 A1, date not available.
English language DERWENT abstract of EP 0 984 025 A2, date not available.
English language DERWENT abstract of EP 1 002 514 A1, date not available.
English language DERWENT abstract of EP 1 031 342 A1, date not available.
English language DERWENT abstract of EP 1 048 282 A1, date not available.
English language DERWENT abstract of EP 1 053 742 A1, date not available.
English language DERWENT abstract of EP 1 064 919 A1, date not available.
English language DERWENT abstract of EP 1 064 920 A1, date not available.
English language DERWENT abstract of EP 1 066 814 A1, date not available.
English language DERWENT abstract of EP 1 068 854 A1, date not available.
English language DERWENT abstract of EP 1 068 855 A1, date not available.
English language DERWENT abstract of EP 1 086 945 A1, date not available.
English language DERWENT abstract of EP 1 090 627 B1, date not available.
English language DERWENT abstract of EP 1 114 636 A1, date not available.
English language DERWENT abstract of FR 2 232 303, date not available.
English language DERWENT abstract of FR 2 674 126, date not available.
English language DERWENT abstract of FR 2 785 179, date not available.
English language DERWENT abstract of FR 2 796 272, date not available.
English language DERWENT abstract of FR 2 796 273, date not available.
English language DERWENT abstract of FR 2 802 806, date not available.
English language DERWENT abstract of FR 2 804 017, date not available.
English language DERWENT abstract of FR 2 804 018, date not available.
English language DERWENT abstract of FR 2 810 562, date not available.
English language DERWENT abstract of FR 2 811 225, date not available.
English language DERWENT abstract of FR 2 817 739, date not available.
English language DERWENT abstract of FR 2 817 740, date not available.
English language DERWENT abstract of FR 2 817 743, date not available.
English language DERWENT abstract of FR 2 819 399, date not available.
English language DERWENT abstract of FR 2 819 400, date not available.
English language DERWENT abstract of FR 2 819 402, date not available.
English language DERWENT abstract of JP 04/346909, date not available.
English language DERWENT abstract of JP 10/120903, date not available.
English language DERWENT abstract of JP 10/259344, date not available.
English language DERWENT abstract of JP 11/106216, date not available.
English language DERWENT abstract of JP 11/335228, date not available.
English language DERWENT abstract of JP 11/335242, date not available.
English language DERWENT abstract of JP 11/335254, date not available.
English language DERWENT abstract of JP 2/127568, date not available.
English language DERWENT abstract of JP 2000038314 A, date not available.
English language DERWENT abstract of JP 2000038316 A and JP 2000038317 A, date not available.
English language DERWENT abstract of JP 2000038321 A, date not available.
English language DERWENT abstract of JP 2000086427 A, date not available.
English language DERWENT abstract of JP 2000086429 A, date not available.
English language DERWENT abstract of JP 2000086438 A, date not available.
English language DERWENT abstract of JP 2/216279, date not available.
English language DERWENT abstract of JP 3/014683, date not available.
English language DERWENT abstract of JP 7/179795, date not available.
English language DERWENT abstract of JP 7/267827, date not available.
English language abstract of JP 8/225316 from Patent Abstracts of Japan, date not available.
English language DERWENT abstract of JP 9/20631, date not available.
English language DERWENT abstract of JP 9/295922, date not available.
French Search Report in FR 0016180, dated Oct. 16, 2001.
French Search Reprt in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
Handbook of Cosmetic Science and Tech. Elsevier Advanced Tech., 1st Edition (1994), pp. 1-32.
International Search Report in PCT/FR01/00229, dated Apr. 18, 2001.
International Search Report in PCT/FR01/01958, dated Oct. 26, 2001.
International Search Report in PCT/FR01/03726, dated Apr. 18, 2002.
International Search Report in PCT/FR01/03937, dated Apr. 23, 2002.
International Search Report in PCT/FR01/03938, dated Jun. 10, 2002.
International Search Report in PCT/FR01/03939 (priority document for FR 0016164), dated Apr. 15, 2002.
International Search Report in PCT/FR01/03940 (priority document for FR 0016161), dated Mar. 13, 2002.
International Search Report in PCT/FR01/03945 (priority document for FR 0016163), dated May 31, 2002.
International Search Report in PCT/FR02/00129, dated Jun. 14, 2002.
International Search Report in PCT/FR02/00144 (priority document for FR 0100479), dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.

International Search Report in PCT/IB01/02780, dated Apr. 10, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47459, dated Feb. 6, 2003.
International Search Report in PCT/US 01/47496, dated Feb. 26, 2003.
International Search Report in PCT/US 01/47497, dated Dec. 2, 2002.
Kirk-Othmer, " Encyclopedia of Chemical Technology", Third Edition, vol. 22, John Wiley & Sons, 1983, p. 332-342.
PCT Application No. PCT/US03/41618; Title: Cosmetic Compositions Comprising a Structuring Agent, Silicone Powder and Swelling Agent Inventor: Shao Xiang Lu, Terry Van Liew, Nathalie Geffroy-Hyland International Filing Date: Dec. 22, 2003.
PCT Application No. PCT/US04/01071; Title: Long Wear Cosmetic Composition Inventor: Balanda ATIS International Filing Date: Jan. 16, 2004.
Yasuda et al., "Novel Low-molecular-weight Organic Gels: N,N', N"-Tristearyltrimesamide/Organic Solvent System," Chemistry Letters, pp. 575-576, 1996, the month of publication is not available.
Estee-Lauder MagnaScopic® Maximum Volume mascara product packaging, believed to have first been sold in 2003.
Origins Full Story™ Lush lash mascara product packaging, believed to have first been sold in 2003.

* cited by examiner

COSMETIC COMPOSITIONS CONTAINING AT LEAST ONE HETEROPOLYMER AND AT LEAST ONE GELLING AGENT AND METHODS OF USING THE SAME

The present invention relates to a care and/or treatment and/or make-up composition for the skin, including the scalp, and/or for the lips of human beings, and/or for keratinous materials, such as keratinous fibers, containing a liquid fatty phase, structured with a specific polymer containing a hetero atom. This composition can be stable over time and may be in the form of a tube or stick of make-up such as lipstick, the application of which can produce a glossy deposit with good staying power or long-wearing properties.

It is common to find a structured, i.e., gelled and/or rigidified, liquid fatty phase in cosmetic or dermatological products; this is especially the case in solid compositions such as deodorants, lip balms, lipsticks, concealer products, eyeshadows and cast foundations. This structuring may be obtained with the aid of waxes and/or fillers. Unfortunately, these waxes and fillers may have a tendency to make the composition matte, which may not always be desirable, in particular for a lipstick or an eyeshadow. Consumers are always on the lookout for a lipstick in stick form which can deposit a film with good staying power or long wearing properties but which is also increasingly glossy.

For the purposes of the invention, the expression "liquid fatty phase" means a fatty phase which is liquid at room temperature (25° C.) and atmospheric pressure (760 mmHg, i.e. 101 KPa), composed of one or more fatty substances that are liquid at room temperature, also referred to as oils, that are generally mutually compatible, i.e. forming a homogeneous phase macroscopically. The expression "liquid fatty substance" means a non-aqueous liquid medium which is immiscible in all proportions with water, for example, a hydrocarbon-based compound comprising one or more carbon chains each containing at least 5 carbon atoms and possibly comprising at least one polar group chosen from carboxylic acid, hydroxyl, polyol, amine, amide, phosphoric acid, phosphate, ester, ether, urea, carbamate, thiol, thioether and thioester, a silicone compound optionally comprising carbon chains at the end or pendant, these chains optionally being substituted with a group chosen from fluoro, perfluoro, (poly)amino acid, ether, hydroxyl, amine, acid and ester groups; or a fluoro or perfluoro compound such as fluorohydrocarbons or perfluorohydrocarbons containing at least 5 carbon atoms, possibly comprising a hetero atom chosen from N, O, S and P and optionally at least one function chosen from ether, ester, amine, acid, carbamate, urea, thiol and hydroxyl groups.

The structuring of the liquid fatty phase may make it possible in particular to limit its exudation (or syneresis) from solid compositions, particularly in hot and humid areas and, furthermore, after deposition on the skin or the lips, to limit the migration of this phase into wrinkles and fine lines, a characteristic particularly desirable in a lipstick or eyeshadow. The reason for this is that considerable migration of the liquid fatty phase, particularly when it is charged with coloring agents, may lead to an unpleasant appearance around the lips and the eyes, making wrinkles and fine lines particularly prominent. Consumers often state this migration as being a major drawback of conventional lipsticks and eyeshadows. The term "migration" means movement of the composition beyond its initial site of application.

Gloss of a lipstick or other cosmetic is generally associated with the nature of the liquid fatty phase. Thus, it may be possible to reduce the amount of waxes and/or fillers in the composition in order to increase the gloss of a lipstick, but in that case the migration of the liquid fatty phase may increase. In other words, the amounts of waxes and of fillers required to prepare a stick of suitable hardness which does not exude at room temperature are a restricting factor on the gloss of the deposit.

To overcome at least one of these drawbacks, the inventors have envisaged replacing all or some of the waxes and/or fillers with polymers for structuring the liquid fatty phase, of the polyamide, polyurea or polyurethane type. Unfortunately, the sticks obtained have a greater or lesser tendency to exude.

Furthermore, make-up compositions should have good staying power or long-wearing properties over time, i.e., little turning of or change in color over time or a gradual or homogeneous change of the deposit over time. The turning of or change in color of the deposit may be due, for lipsticks, to an interaction with saliva and, for foundations and eyeshadows, to an interaction with the sweat and sebum secreted by the skin. Specifically, a composition which has no staying power or long wearing properties may oblige the user to reapply make-up regularly. However, consumers nowadays wish to enhance the beauty of their face or body while spending as little time as possible in doing so.

The need thus remains for a composition which does not have at least one of the above drawbacks, which has good stability over time, even in hot and humid countries, and which produces a deposit on the skin or the lips that shows good staying power or long-wearing over time and has a glossy appearance. Furthermore, this composition can be easy to manufacture and can give the deposit a sensation of not drying out, both during application and over time.

One subject of the invention is a care and/or make-up and/or treatment composition for the skin and/or the lips of the face and/or for superficial body growths, i.e., keratinous materials, such as nails or keratinous fibers, which makes it possible to overcome at least one of the drawbacks mentioned above.

The inventors have found, surprisingly, that the use of at least one specific polymer combined with at least one gelling agent for a liquid fatty phase makes it possible to obtain a stick whose application to the lips produces a deposit which can have noteworthy cosmetic properties. In particular, the deposit can be at least one of glossy, supple, comfortable and "migration-resistant". Furthermore, the composition can be stable over time and has been observed not to exude at room temperature.

The term "stable" refers to a composition which has been observed not to exude at room temperature (25° C.) for at least 2 months, for example, at least 9 months.

The invention applies not only to make-up products for the lips, such as lipsticks, lip glosses and lip pencils, but also to care and/or treatment products for the skin, including the scalp, and for the lips, such as antisun care products for the human face, the body or the lips, such as in stick form, make-up removing products for the skin of the face and body, make-up products for the skin, both of the human face and body, such as foundations optionally cast in stick or dish form, concealer products, blushers, eyeshadows, face powders, transfer tattoos, body hygiene products (i.e., products which do not relate to the care, make-up, or treatment of keratin materials) such as deodorant, e.g., in stick form, shampoos, conditioners and make-up products for the eyes such as eyeliners, eye pencils and mascaras, e.g., in cake form, as well as make-up and care products for superficial body growths, for instance keratinous fibers such as the hair, the eyelashes, and the eyebrows or nails.

Another aspect of the invention is a structured composition comprising at least one liquid fatty phase comprising (i) at least one structuring polymer comprising a polymer skeleton having hydrocarbon-based repeating units containing at least one hetero atom, and (ii) at least one gelling agent for the liquid fatty phase. As used herein, the expression "at least one" means one or more and thus includes individual components as well as mixtures/combinations.

The composition of the invention can be in the form of a paste, a solid or a more or less viscous cream. It can be a single or multiple emulsion, such as an oil-in-water or water-in-oil emulsion or an oil-in-water-in-oil emulsion, or a water-in-oil-in-water emulsion, or a rigid or soft gel containing an oily continuous phase. For example, the liquid fatty phase can be the continuous phase of the composition. In one embodiment, the composition is anhydrous. In one embodiment, the composition is in a form cast as a stick or in a dish, for example solid, and further example, in the form of an oily rigid gel, such as an anhydrous gel, e.g., an anhydrous stick. In a further embodiment, the composition is in the form of an opaque or translucent rigid gel (depending on the presence or absence of pigments), and in a specific example, the liquid fatty phase forms the continuous phase. In one embodiment, the composition is chosen from molded and poured sticks.

The structuring of the liquid fatty phase can be modified depending on the nature of the polymer containing a hetero atom and the gelling agent that are used, and may be such that a rigid structure in the form of a stick is obtained. When these sticks are coloured, they make it possible, after application, to obtain a uniformly coloured and glossy deposit which does not migrate and/or which has good staying power, in particular of the colour over time.

The composition of the invention can be a composition for the lips, such as a lipstick composition in stick form.

Structuring Polymer

In one embodiment, the at least one structuring polymer in the composition of the invention is a solid that is not deformable at room temperature (25° C.) and atmospheric pressure (760 mmHg, i.e. 101 KPa). In a further embodiment, the at least one structuring polymer is capable of structuring the composition without opacifying it. The inventor think that is due to the fact that the polymer does not crystallize. Moreover, the structuration of the liquid fatty phase is due to hydrogen interactions between two molecules of polymer and/or between the polymer and the liquid fatty phase. As defined above, the at least one structuring polymer of the present invention comprises a polymer skeleton comprising at least one hydrocarbon-based repeating unit comprising at least one hetero atom. In one embodiment, the at least one structuring polymer further comprises at least one terminal fatty chain chosen from alkyl and alkenyl chains, such as of at least 4 atoms, and further such as comprising 8 to 120 carbon atoms, bonded to the polymer skeleton via at least one linking group. The terminal fatty chain may, for example, be functionalized. The at least one structuring polymer may also comprise at least one pendant fatty chain chosen from alkyl and alkenyl chains, such as of at least 4 atoms, and further such as comprising 8 to 120 carbon atoms, bonded to any carbon or hetero atom of the polymer skeleton via at least one linking group. The pendant fatty chain may, for example, be functionalized. The at least one structuring polymer may comprise both at least one pendant fatty chain and at least one terminal fatty chain as defined above, and one or both types of chains can be functionalized.

In one embodiment, the structuring polymer comprises at least two hydrocarbon-based repeating units. As a further example, the structuring polymer comprises at least three hydrocarbon-based repeating units and as an even further example, the at least three repeating units are identical.

As used herein, "functionalized" means comprising at least one functional group. Non-limiting examples of functional groups include hydroxyl groups, ether groups, oxyalkylene groups, polyoxyalkylene groups, carboxylic acid groups, amine groups, amide groups, halogen containing groups, including fluoro and perfluoro groups, halogen atoms, ester groups, siloxane groups and polysiloxane groups.

For purposes of the invention, the expression "functionalized chain" means, for example, an alkyl chain comprising at least one functional (reactive) group chosen, for example, from those recited above. For example, in one embodiment, the hydrogen atoms of at least one alkyl chain may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units, such as, for example, a compound containing at least 3 repeating units, which may be identical.

As used herein, the expression "hydrocarbon-based repeating unit" includes a repeating unit comprising from 2 to 80 carbon atoms, such as, for example, from 2 to 60 carbon atoms. The at least one hydrocarbon-based repeating unit may also comprise oxygen atoms. The hydrocarbon-based repeating unit may be chosen from saturated and unsaturated hydrocarbon-based repeating units which in turn may be chosen from linear hydrocarbon-based repeating units, branched hydrocarbon-based repeating units and cyclic hydrocarbon-based repeating units. The at least one hydrocarbon-based repeating unit may comprise, for example, at least one hetero atom that is part of the polymer skeleton, i.e., not pendant. The at least one hetero atom may be chosen, for example, from nitrogen, sulphur, and phosphorus. For example, the at least one hetero atom may be a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

The at least one repeating unit comprising at least one hetero atom may be chosen, for example, from amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the hetero atoms of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the composition of the invention comprises at least one structuring polymer with nitrogen atoms, such as amide, urea, or carbamate units, and at least one polar oil.

In one embodiment, in the at least one structuring polymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one structuring polymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depends on the nature of a liquid fatty phase of the composition and is, for example, similar to the nature of the fatty phase. For example, not to be limited as to theory, the more polar the hydrocarbon-based repeating units containing a hetero atom, and in high proportion, which corresponds to the presence of several hetero atoms, the greater the affinity of the at least one structuring polymer to polar oils. Conversely, the more non-polar, or even apolar, and lesser in proportion the hydrocarbon-based repeating units containing a hetero atom, the greater the affinity of the polymer for apolar oils.

In another embodiment, the invention is drawn to a structured composition containing at least one liquid fatty phase structured with at least one structuring polymer, wherein the at least one structuring polymer is a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The liquid fatty phase further contains at least one gelling agent for gelling the liquid fatty phase. The at least one liquid fatty phase, the at least one structuring polyamide and the at least one gelling agent together form a physiologically acceptable medium.

When the structuring polymer has amide repeating units, the pendant fatty chains may be linked to at least one of the nitrogen atoms in the amide repeating units.

The structuring polymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

However, this weight-average molecular mass can represent up to 500 000 and even up to 1 000 000. The structuring polymer, as for example the polyamide polymer, is non soluble in water or in aqueous phase. In another embodiment, the structuring polymer has no ionic group.

As discussed, the at least one structuring polymer may, for example, be chosen from polyamide polymers. A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via the at least one linking group. In one embodiment, the at least one linking group is chosen from single bonds and urea, urethane, thiourea, thiourethane, thioether, thioester, ester, ether and amine groups. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The at least one dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, and phenylenediamine and from triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the at least one polyamide polymer may be chosen from those described in U.S. Pat. No. 5,783,657, the disclosure of which is incorporated herein by reference, which are polyamide polymers of formula (I):

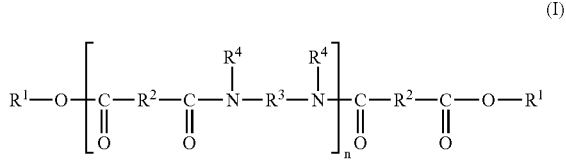

(I)

in which:
- n is an integer which represents the number of amide units such that the number of ester groups present in the at least one polyamide polymer ranges from 10% to 50% of the total number of all the ester groups and all the amide groups comprised in the at least one polyamide polymer;
- $R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;
- $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
- $R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
- $R^4$, which are identical or different, are each chosen from hydrogen atoms, $C_1$ to $C_{10}$ alkyl groups and a direct bond to at least one group chosen from $R^3$ and another $R^4$ such that when the at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In the polymer of formula (I), the terminal fatty chains that are optionally functionalized for the purposes of the invention are terminal chains linked to the last hetero atom, in this case nitrogen, of the polyamide skeleton.

In one embodiment, the ester groups of formula (I), which form part of the terminal and/or pendant fatty chains for the purposes of the invention, are present in an amount ranging from 15% to 40% of the total number of ester and amide groups (i.e., heteroatom groups), such as from 20% to 35%.

In formula (I), in one embodiment, n may be an integer ranging from 1 to 10, for example from 1 to 5, and as further example an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ hydrocarbon-based, e.g., alkylene groups. At least 50% of all $R^2$, for example at least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{18}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms.

As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of an at least one polyamide polymer which may be used in the composition according to the present invention include the commercial products sold by Arizona Chemical under the names Uniclear 80 and Uniclear 100. These are sold or made, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of an at least one polyamide polymer which may be used in the compositions according to the present invention include polyamide polymers (or polyamide resins) resulting from the condensation of at least one aliphatic dicarboxylic acid and at least one diamine, the carbonyl and amine groups being condensed via an amide bond. In one embodiment, these polymers contain more than two carbonyl groups and more than two amine groups. Examples of these polyamide polymers are those sold or made under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6000 to 9000. For further information regarding these polyamides, reference may be made to U.S. Pat. Nos. 3,645,705 and 3,148,125, the disclosures of which are hereby incorporated by reference. In one embodiment, Versamid 930 or 744 may be used.

Other examples of polyamides include those sold or made by the company Arizona Chemical under the references Uni-Rez (2658, 2931, 2970, 2621, 2613, 2624, 2665, 1554, 2623 and 2662) and the product sold or made under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

The at least one structuring polymer in the compositions of the invention may have a softening point greater than 50° C., such as from 65° C. to 190° C., and for example less than 150° C., and further such as from 70° C. to 130° C., and even further such as from 80° C. to 105° C. This softening point may be lower than that of structuring polymers used in the art which may facilitate the use of the at least one structuring polymer of the present invention and may limit the degradation of the liquid fatty phase. These polymers may be non waxy polymers.

The softening point can be measured by a well known method as "Differential Scanning Calorimetry" (i.e. DSC method) with a temperature rise of 5 to 10° C./min.

In one embodiment, the at least one structuring polymer in the composition according to the invention corresponds to the polyamide polymers of formula (I). Due to fatty chain(s), these polymers may be readily soluble in oils and thus lead to compositions that are macroscopically homogeneous even with a high content (at least 25%) of at least one structuring polymer, unlike polymers not containing a fatty chain.

The at least one structuring polymer may be present in the composition in an amount ranging, for example, from 0.5% to 80% by weight relative to the total weight of the composition, such as for example 2% to 60%, and further, for example, from 5 to 40%. In a further embodiment the at least one structuring polymer may be present in the composition in an amount ranging, for example, from 5% to 25% by weight relative to the total weight of the composition.

In one embodiment, when the at least one structuring polymer of the present invention comprises a urea urethane having the following formula:

R—O—CO—NH—R'—NH—CO—NH—R"—NH—CO—NH—R'—NH—CO—OR then R represents $C_nH_{2n+1}$, wherein n represents an integer having a value greater than 22, for example from 23 to 120, and further, for example from 23 to 68, or $C_mH_{2m+1}(OC_pH_{2p})_r$—, wherein m represents an integer having a value of greater than 18, for example from 19 to 120, and further, for example, from 23 to 68, p represents an integer having a value of from 2 to 4, and r represents an integer having a value of from 1 to 10, R' represents:

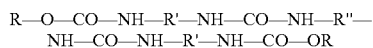

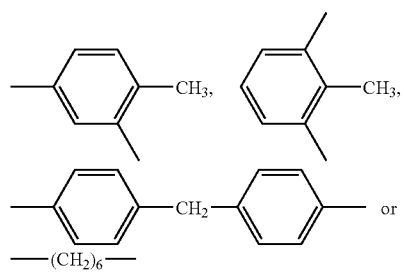

and R" represents:

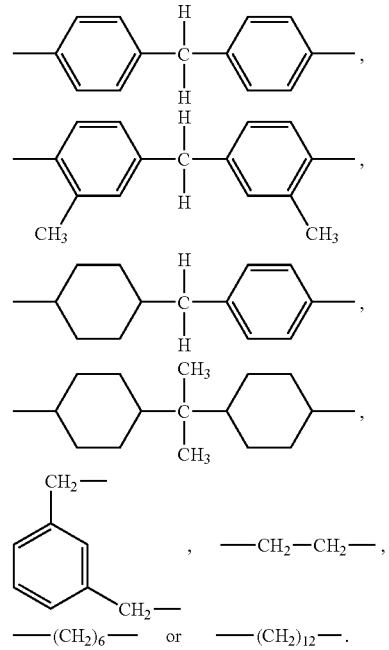

In one embodiment of the invention, the at least one structuring polymer is not modified urea-urethane of the type available as BYK 410. In another embodiment of the invention, the at least one gelling agent is not modified urea-urethane of the type available as BYK 410.

In another embodiment of the invention, the present invention is drawn to a structured composition comprising at least one liquid fatty phase structured with at least one structuring polymer comprising a polymer skeleton comprising at least one hydrocarbon-based repeating unit comprising at least one hetero atom, wherein the at least one structuring polymer further comprises at least one terminal fatty chain, optionally functionalized, chosen from alkyl and alkenyl chains, such as alkyl and alkenyl chains having at least four carbon atoms, and further such as alkyl and alkenyl chains comprising from 8 to 120 carbon atoms, bonded to the polymer skeleton via at least one linking group chosen from amides, ureas, and esters, wherein when the at least one linking group is chosen from esters, the at least one terminal fatty chain is chosen from branched alkyl groups. The at least one structuring polymer may also comprise at least one pendant fatty chain, optionally functionalized, chosen from alkyl and alkenyl chains, such as alkyl and alkenyl chains having at least four carbon atoms, and further such as alkyl and alkenyl chains comprising from 8 to 120 carbon atoms, bonded to any carbon or hetero atom of the polymer skeleton via at least one linking group chosen from amides, ureas, and esters, wherein when the at least one linking group is chosen from esters, the at least one terminal fatty chain is chosen from branched alkyl groups. The at least one structuring polymer may comprise both at least one pendant fatty chain and at least one terminal fatty chain as defined above in this paragraph.

Further, an embodiment of the invention relates to a skin, lip, or keratinous fiber care, treatment, or make-up composition comprising a structured composition containing at least one liquid fatty phase structured with at least one structuring polymer comprising a polymer skeleton comprising at least one hydrocarbon-based repeating unit comprising at least one hetero atom and at least one gelling agent for gelling the liquid fatty phase.

Additionally, an embodiment of the invention relates to a skin, lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom, at least one gelling agent for gelling the liquid fatty phase, and at least one coloring agent.

Additionally, an embodiment of the invention relates to a care and/or treatment and/or make-up composition for keratin materials comprising a composition containing at least one liquid fatty phase which comprises (i) at least one structuring polymer comprising a polymer skeleton which comprises at least one hydrocarbon-based repeating unit comprising at least one hetero atom; and (ii) at least one gelling agent, wherein said at least one gelling agent is not stearalkonium hectorite.

Another embodiment of the invention relates to a mascara, an eyeliner, a foundation, a lipstick, a blusher, a make-up-removing product, a make-up product for the body, an eyeshadow, a face powder, a concealer product, a shampoo, a conditioner, an antisun product or a care product for the lips, skin, or hair comprising a composition comprising at least one liquid fatty phase in the mascara, eyeliner, foundation, lipstick, blusher, make-up-removing product, make-up product for the body, eyeshadow, face powder, concealer product, shampoo, conditioner, antisun product or care product for the skin, lips, or hair which comprises:

(i) at least one structuring polymer comprising:

a polymer skeleton which comprises at least one hydrocarbon-based repeating unit comprising at least one hetero atom; and (ii) at least one gelling agent.

Another embodiment of the invention relates to a deodorant product or a care product for the skin or body comprising an anhydrous composition comprising at least one liquid fatty phase in the product which comprises:

(i) at least one structuring polymer comprising:

a polymer skeleton which comprises at least one hydrocarbon-based repeating unit comprising at least one hetero atom; and (ii) at least one gelling agent.

Another embodiment of the invention relates to a lip composition comprising an anhydrous composition comprising at least one liquid fatty phase in the product which comprises:

(i) at least one structuring polymer comprising:

a polymer skeleton which comprises at least one hydrocarbon-based repeating unit comprising at least one hetero atom; and (ii) at least one gelling agent.

Another embodiment of the invention relates to a lipstick composition in stick form comprising at least one continuous liquid fatty phase, at least one gelling agent for the fatty phase and at least one non-waxy structuring polymer having a weight-average molecular mass of less than 100 000, the continuous liquid fatty phase, the at least one gelling agent for the fatty phase and the at least one non-waxy structuring polymer being present in the lipstick composition.

Another embodiment of the invention relates to a method for care, make-up or treatment of keratin materials comprising applying to the keratin materials an anhydrous composition comprising at least one liquid fatty phase which comprises:

(i) at least one structuring polymer comprising:

a polymer skeleton which comprises at least one hydrocarbon-based repeating unit comprising at least one hetero atom; and (ii) at least one gelling agent wherein said at least one gelling agent is not stearalkonium hectorite.

Another embodiment of the invention relates to a method for care, make-up or treatment of keratinous fibers, lips, or skin comprising applying to the keratinous fibers, lips, or skin a composition comprising at least one liquid fatty phase which comprises:

(i) at least one structuring polymer comprising:

a polymer skeleton which comprises at least one hydrocarbon-based repeating unit comprising at least one hetero atom; and (ii) at least one gelling agent.

Another embodiment of the invention relates to a method for providing an anhydrous composition having at least one property chosen from non-exudation, gloss, and comfortable deposit on keratin materials chosen from lips, skin, and keratinous fibers, comprising including in the composition at least one liquid fatty phase which comprises:

(i) at least one structuring polymer comprising:

a polymer skeleton which comprises at least one hydrocarbon-based repeating unit comprising at least one hetero atom; and (ii) at least one gelling agent.

Another embodiment of the invention relates to a an anhydrous composition comprising at least one liquid fatty phase which comprises:

(i) at least one structuring polymer comprising:

a polymer skeleton which comprises at least one hydrocarbon-based repeating unit comprising at least one hetero atom; and (ii) at least one gelling agent, wherein the at least one structuring polymer or the at least one gelling agent is not a compound of formula (II)

$$R-O-CO-NH-R'-NH-CO-NH-R''-NH-CO-NH-R'-NH-CO-OR \quad (II)$$

wherein R represents $C_nH_{2n+1}-$ or $C_mH_{2m+1}(C_pH_{2p}O)_r-$; n represents an integer having a value of from 4 to 22; m represents an integer having a value of from 1 to 18; p represents an integer having a value of from 2 to 4; and r represents an integer having a value of from 1 to 10;

R' represents:

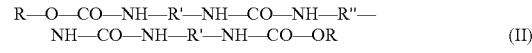

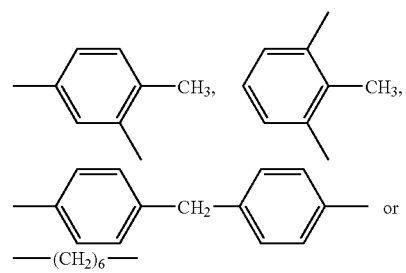

and R" represents:

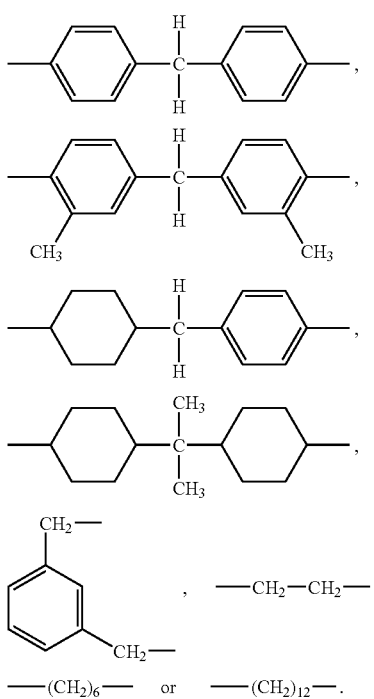

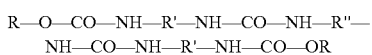

Another embodiment of the invention relates to a method of making up or caring for skin, lips keratinous fibers comprising applying to the skin, lips, or keratinous fibers a structured composition containing at least one liquid fatty phase structured with at least one structuring polymer comprising a polymer skeleton comprising at least one hydrocarbon-based repeating unit comprising at least one hetero atom and at least one gelling agent for gelling the liquid fatty phase.

Another embodiment of the invention relates to an anhydrous composition comprising at least one liquid fatty phase which comprises:

(i) at least one structuring polymer comprising:

a polymer skeleton which comprises at least three hydrocarbon-based repeating units comprising at least one hetero atom; and (ii) at least one gelling agent, and for example, the at least three hydrocarbon-based repeating units can be identical.

Another embodiment of the invention relates to a composition comprising at least one liquid fatty phase which comprises:

(i) at least one structuring polymer chosen from urea urethanes having the following formula:

R—O—CO—NH—R'—NH—CO—NH—R"—
NH—CO—NH—R'—NH—CO—OR wherein R represents $C_nH_{2n+1}$—, wherein n represents an integer having a value greater than 22 or $C_mH_{2m+1}(OC_pH_{2p})_r$—, wherein m represents an integer having a value of greater than 18, p represents an integer having a value of from 2 to 4, and r represents an integer having a value of from 1 to 10, R' represents:

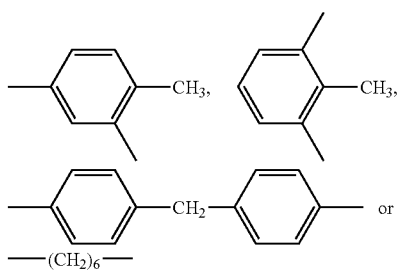

and R" represents:

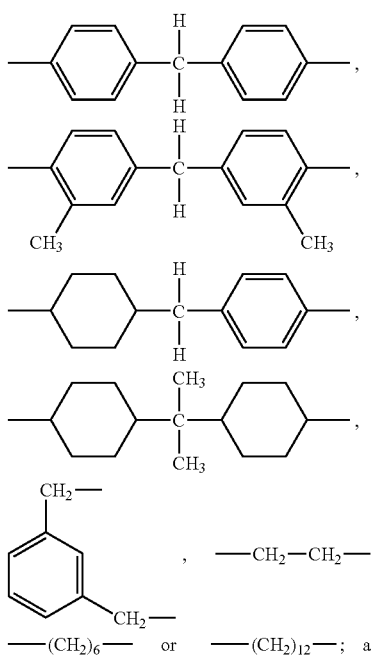

(ii) at least one gelling agent.

Another embodiment of the invention relates to a composition comprising at least one liquid fatty phase which comprises:

(i) at least one structuring polymer comprising a polymer skeleton which comprises at least one hydrocarbon-based repeating unit comprising at least one hetero atom with the proviso that the at least one hetero atom is not nitrogen; and (ii) at least one gelling agent.

In another embodiment, the structuring polymer has the formula (II).

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2 i. from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, and further such as from 30 gf to 200 gf.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within the scope of the invention.

As is evident, the hardness of the composition according to the invention may, for example, be such that the composition is advantageously self-supporting and can disintegrate easily to form a satisfactory deposit on the skin and/or the lips and/or superficial body growths, such as keratinous fibres. In addition, with this hardness, the composition of the invention may have good impact strength.

According to the invention, the composition in stick form may have the behavior of a deformable, flexible elastic solid, giving noteworthy elastic softness on application. The compositions in stick form of the prior art do not have these properties of elasticity and flexibility.

Amphiphilic Compound

The polymer can be combined with at least one amphiphilic compound that is liquid and non-volatile at room temperature, having a hydrophilic/lipophilic balance (HLB) of less than 12, such as from 1 to 8 and further such as from 1 to 5. According to the invention, one or more amphiphilic compounds may be used. The aim of these amphiphilic compounds is to reinforce the structuring properties of the polymer containing a hetero atom, to facilitate the use of the polymer and to improve the ability of the stick or tube to be deposited. However, it is possible to obtain a stick with good mechanical and/or thermal properties without including at least one amphiphilic compound.

The at least one amphiphilic compound which can be used in the composition of the invention may, for example, comprise a lipophilic part linked to a polar part, the lipophilic part comprising a carbon-based chain containing at least 8 carbon atoms, for example from 18 to 32 carbon atoms or from 18 to 28 carbon atoms. The polar part of the at least one amphiphilic compound may, in one embodiment, be the residue of a compound chosen from alcohols and polyols containing from 1 to 12 hydroxyl groups, and polyoxyalkylenes comprising at least 2 oxyalkylene units and containing from 0 to 20 oxypropylene units and/or from 0 to 20 oxyethylene units. For example, the at least one amphiphilic compound may be an ester chosen from the hydroxystearates, oleates and isostearates of glycerol, of sorbitan and of methylglucose, and from branched $C_{12}$ to $C_{26}$ fatty alcohols such as octyldodecanol. Among these esters, monoesters and mixtures of mono- and diesters can also be used.

The respective contents of lipophilic gelling agent and of polymer containing a hetero atom and optionally that of the amphiphilic compound are chosen according to the desired hardness of the composition and as a function of the specific application envisaged.

The respective amounts of polymer, of gelling agent and optionally of amphiphilic compound should be such that they produce a stick which can be worn down. In practice, the amount of polymer represents, for example, from 0.5% to 80% of the total weight of the composition, such as from 2 to 60% and further such as from 5% to 40%. The amount of amphiphilic compound in practice represents, for example, from 0.1% to 35% of the total weight of the composition, for example from 1% to 20% and as a further example, from 1% to 15%, if it is present.

The at least one gelling agent and/or the at least one structuring polymer have an affinity with the fatty phase and in particular with a chemical portion of one of the oils forming the liquid fatty phase of the composition so that physical links with the oils, such as hydrogen bonds, are formed.

In one embodiment, the gelling agent is not chosen from any of silica, methyl 12-hydroxystearate, 12-hydroxy stearic acid, and stearalkonium hectorite.

Liquid Fatty Phase

The at least one liquid, in one embodiment, may comprise at least one oil. In one embodiment, at least one oil has an affinity with the structuring polymer and/or with the gelling agent. The at least one oil, for example, may be chosen from polar oils and apolar olis including hydrocarbon-based liquid oils and oily liquids at room temperature. In one embodiment, the composition of the invention comprises at least one structuring polymer and at least one polar oil. The polar oils of the invention, for example, may be added to the apolar oils, the apolar oils acting in particular as co-solvent for the polar oils.

According to the invention, the structuring of the at least one liquid fatty phase may be obtained with the aid of at least one polymer of formula (I). In general, the polymers of formula (I) may be in the form of mixtures of polymers, these mixtures also possibly containing a synthetic product corresponding to a compound of formula (I) in which n is 0, i.e., a diester.

The liquid fatty phase of the composition may contain more than 30%, for example, more than 40%, of liquid oil(s) containing a group similar to that of the units containing a hetero atom of the structuring polymer, and for example from 50% to 100%. In one embodiment, the liquid fatty phase structured with a polyamide-type skeleton contains a high quantity, i.e., greater than 30%, for example greater than 40% relative to the total weight of the liquid fatty phase, or from 50% to 100%, of at least one apolar, such as hydrocarbon-based, oil. For the purposes of the invention, the expression "hydrocarbon-based oil" means an oil essentially comprising carbon and hydrogen atoms, optionally with at least one group chosen from hydroxyl, ester, carboxyl and ether groups. With such a fatty phase, the at least one gelling agent may, for example, contain an amine, amide or urethane group.

For a liquid fatty phase structured with a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase. In this embodiment, the at least one gelling agent may comprise a silicone group.

For a liquid fatty phase structured with an apolar polymer of the hydrocarbon-based type, this fatty phase may contain more than 30%, for example more than 40% by weight, or from 50% to 100% by weight, of at least one liquid apolar, such as hydrocarbon-based, oil, relative to the total weight of the liquid fatty phase. In this embodiment, the at least one gelling agent may contain hydrocarbon groups chosen from linear, branched and cyclic hydrocarbon-based groups, such as $C_1$ to $C_{40}$ groups.

For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils can be chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6 \geq 10$, such as, for example, purcellin oil (cetostearyl octanoate), isononyl isononanoate, $C_{12}$-$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;

$C_8$ to $C_{26}$ fatty alcohols such as oleyl alcohol; and $C_8$ to $C_{26}$ fatty acids such as oleic acid, linolenic acid or linoleic acid.

The at least one apolar oil according to the invention is chosen from, for example, silicone oils chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane; and mixtures thereof. The structured oils, for example those structured with polyamides such as those of formula (I) or the polyurethanes or polyureas or polyurea-urethanes, may be, in one embodiment, apolar oils, such as an oil or a mixture of hydrocarbon oils chosen from those of mineral and synthetic origin, chosen from hydrocarbons such as alkanes such as Parleam® oil, isoparaffins including isododecane, and squalane, and mixtures thereof.

The structured oils, for example those structured with polyamides such as those of formula (I) or the polyurethanes or polyureas or polyurea-urethanes, may be, in one embodiment, apolar oils, such as an oil or a mixture of hydrocarbon oils chosen from those of mineral and synthetic origin, chosen from hydrocarbons such as alkanes such as hydrogenated polybutene, e.g., Parleam® oil from Nippon Oil Fats, isoparaffins including isododecane, and squalane, and mixtures thereof. These oils may, in one embodiment, be combined with at least one phenylsilicone oil.

The liquid fatty phase, in one embodiment, contains at least one non-volatile oil chosen from, for example, hydrocarbon-based oils of mineral, plant and synthetic origin, synthetic esters or ethers, silicone oils and mixtures thereof.

In practice, the total liquid fatty phase can be, for example, present in an amount ranging from 1% to 99% by weight relative to the total weight of the composition, for example from 5% to 99%, 5% to 95.5%, from 10% to 80% or from 20% to 75%.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ to 300 mmHg (1.33 to 40 000 Pa) and, for example, greater than 0.03 mmHg (4 Pa) and further example greater than 0.3 mmHg (40 Pa). The expression "non-volatile oil" means an oil which remains on the skin or the lips at room temperature and atmospheric pressure for at least several hours, such as those having a vapor pressure of less than $10^{-2}$ mmHg (1.33 Pa).

According to the invention, these volatile solvents may facilitate the staying power or long wearing properties of the composition on the skin, the lips or superficial body growths such as nails and keratinous fibers. The solvents can be chosen from hydrocarbon-based solvents, silicone solvents optionally comprising alkyl or alkoxy groups that are pendant or at the end of a silicone chain, and a mixture of these solvents.

The volatile oil(s), in one embodiment, can be present in an amount ranging from 0% to 95.5% relative to the total weight of the composition, such as from 2% to 75% or, for example, from 10% to 45%. This amount will be adapted by a person skilled in the art according to the desired staying power or long wearing properties.

The at least one liquid fatty phase of the composition of the invention may further comprises a dispersion of lipid vesicles. The composition of the invention may also, for example, be in the form of a fluid anhydrous gel, a rigid anhydrous gel, a fluid simple emulsion, a fluid multiple emulsion, a rigid simple emulsion or a rigid multiple emulsion. The simple emulsion or multiple emulsion may comprise a continuous phase chosen from an aqueous phase optionally containing dispersed lipid vesicles, or a fatty phase optionally containing dispersed lipid vesicles. In one embodiment, the composition has a continuous oily phase or fatty phase and is more specifically an anhydrous composition in, for example, a stick or dish form. An anhydrous composition is one that has less than 10% water by weight, such as, for example, less than 5% by weight.

Gelling Agent

The composition of the invention also contains at least one lipophilic agent for gelling a liquid fatty phase. This at least one gelling agent is chosen from liposoluble and lipodispersible rheological agents, such as agents that are soluble or dispersible in the fatty phase that is liquid at room temperature and atmospheric pressure. The at least one gelling agent may be chosen from gelling agents in polymeric form and gelling agents in mineral form. In one embodiment, the at least one gelling agent may be in mineral form with particle sizes that cause little or no light scattering. Thus, it may be possible to obtain a translucent or even transparent composition.

In one embodiment, the at least one gelling agent is not soluble in an aqueous phase or in water.

Fatty-phase gelling agents or rheological agents which can be used in the invention may be chosen from lipodispersible mineral particles such as optionally modified clays and optionally modified silica, for example which have been hydrophobic-treated, as well as polymeric gelling agents such as partially or totally crosslinked elastomeric polyorganosiloxanes of three-dimensional structure; galactomannans comprising from 1 to 6 hydroxyl groups, for example 2 to 4 hydroxyl groups, per saccharide, substituted with a saturated or unsaturated alkyl chain; polymers or copolymers resulting from the polymerization or copolymerization of an ethylenic monomer, comprising one or more ethylenic, preferably conjugated bonds (or dienes); silicone gums; ethylcellulose, such as the products sold under the name Ethocel by Dow Chemical; and mixtures thereof.

As modified clays which can be used, mention may be made of hectorites modified with an ammonium chloride of a $C_{10}$ to $C_{22}$ fatty acid, such as hectorite modified with distearyldimethylammonium chloride, also known as quatermium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as steralkonium bentonites, such as the products sold or made under the names Claytone APA and Claytone AF by the company Southern Clay, and Baragel 24 sold or made by the company Rheox.

As polyorganosiloxanes which can be used in the invention, mention may be made of the crosslinked elastomeric polyorganosiloxanes described in application EP-A-0,295,886, the disclosure of which is incorporated herein by reference. According to that application, they are obtained by addition reaction and crosslinking, in the presence of a platinum-type catalyst, of at least:

(a) a polyorganosiloxane having at least two $C_2$ to $C_6$ lower alkenyl groups per molecule; and (b) a polyorganosiloxane having at least two hydrogen atoms linked to a silicon atom per molecule. It is also possible to use the polyorganosiloxanes described in U.S. Pat. No. 5,266,321, the disclosure of which is incorporated by reference herein. According to that patent, they are chosen in particular from:

i) polyorganosiloxanes comprising $R_2SiO$ and $RSiO_{1.5}$ units and optionally $R_3SiO_{0.5}$ and/or $SiO_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;

ii) polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally, these polyorganosiloxanes can comprise from 1 to 40 oxyalkylene groups, such as oxypropylene and/or oxyethylene groups.

As examples of polyorganosiloxanes which can be used according to the invention, mention may be made of those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric. A mixture of these commercial products may also be used.

As alkyl galactomannans which can be used in the invention, mention may be made of guar gum or carob gum alkylated with $C_1$ to $C_{-6}$, for example, $C_1$ to $C_3$ alkyl chains, such as ethyl or propyl guar having a degree of substitution of 2 to 3, for example, of about 2.5 to 2.8, as described in document EP-A-708 114 and sold or made by the company Aqualon under the name N-Hance-AG 200® or N-Hance AG 50®.

As polymers or copolymers resulting from the polymerization or copolymerization of an ethylenic monomer, use may be made of vinyl, acrylic or methacrylic copolymers which may be block copolymers, such as diblock or triblock copolymers, or even multiblock or starburst or radial copolymers. The at least one ethylenic gelling agent may comprise, for example, a styrene block (S), an alkylstyrene block (AS), an ethylene/butylene block (EB), an ethylene/propylene block (EP), a butadiene block (B), an isoprene block (I), an acrylate block (A), a methacrylate block (MA) or a combination of these blocks.

In one embodiment, a copolymer comprising at least one styrene block is used as gelling agent or ethylenic rheological agent. A triblock copolymer and in particular those of the polystyrene/polyisoprene or polystyrene/polybutadiene type, such as those sold or made under the name "Luvitol HSB" by BASF and those of the polystyrene/copoly(ethylene-propylene) type or alternatively of the polystyrene/copoly(ethylene/butylene) type, such as those sold or made under the brand name "Kraton" by Shell Chemical Co. or Gelled Permethyl 99A by Penreco, may be used. Styrene-methacrylate copolymers can also be used.

As ethylenical rheological agent which can be used in the composition of the invention, mention may be made, for example, of Kraton (G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton G1750X (EP) multiarm, Kraton G1765X (EP) multiarm, Kraton D-1101 (SBS), Kraton D-1102 (SBS), Kraton D-1107 (SIS), Gelled Permethyl 99A-750, Gelled Permethyl 99A-753-58 (mixture of starburst block polymer and triblock polymer), Gelled Permethyl 99A-753-59 (mixture of starburst block polymer and triblock polymer), Versagel 5970 and Versagel 5960 from Penreco (mixture of starburst polymer and triblock polymer in isododecane), and OS 129880, OS 129881 and OS 84383 from Lubrizol (styrene-methacrylate copolymer).

As other rheological agents which can be used in the invention, mention may be made of silicone gums. The silicone gum can correspond to the formula:

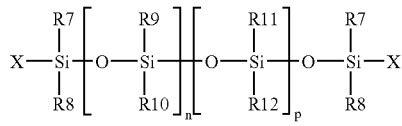

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of greater than 100 000 mPa·s, such as greater than 500 000 mPa·s.

In general, n and p can each take values ranging from 0 to 5 000, such as from 0 to 3 000.

Among the silicone gums which can be used according to the invention, mention may be made of those for which:
- the substituents $R_7$ to $R_{12}$ and X represent a methyl group, p=0 and n=2 700, such as the product sold or made under the name SE30 by the company General Electric,
- the substituents $R_7$ to $R_{12}$ and X represent a methyl group, p=0 and n=2 300, such as the product sold or made under the name AK 500 000 by the company Wacker,
- the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning,
- the substituents $R_7$ to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and
- the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhône-Poulenc (Rhodia Chimie).

As other gelling agents or rheological agents which can be used in the invention, mention may be made of silica, such as fumed silica. The fumed silica may have a particle size which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas which have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be:
- trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot;
- dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot;
- groups derived from reacting fumed silica with silane alkoxides or siloxanes. These treated silicas are, for example, the products sold or made under the reference "Aerosil R805®" by the company Degussa.

According to the invention, a hydrophobic silica, such as a fumed silica, may be used as lipophilic gelling agent or rheological agent. The use of fumed silica makes it possible to obtain a translucent or even transparent composition, in particular in the form of a stick which does not exude, in the absence of opacifying particles such as waxes, fillers and pigments (including nacres).

The at least one liposoluble rheological agent can allow the exudation of the composition to be limited and can allow its stability to be increased, while at the same time conserving the composition's glossy appearance, which is not possible with waxes such as those used conventionally in cosmetics and dermatology. These gelling agents can be used, for example, at concentrations of from 0.05% to 35% relative to the total weight of the composition, for example from 0.5% to 20% or from 1% to 10%.

Additional Additives

The composition of the invention can also comprise any additive usually used in the field under consideration, chosen in particular from antioxidants, essential oils, preserving agents, fragrances, waxes, fillers, products that are pasty or viscous at room temperature, neutralizing agents, liposoluble polymers and polymers that are dispersible in the medium, cosmetic and dermatological active agents such as, for example, emollients, moisturizers, vitamins, essential fatty acids, sunscreens, dispersants such as poly(2-hydroxystearic acid), and mixtures thereof. These additives may be present in the composition in a proportion of from 0% to 20% (such as from 0.01% to 20%) relative to the total weight of the composition and further such as from 0.01% to 10% (if present).

The composition of the invention can also contain, as an additive, an aqueous phase containing water that is optionally thickened or gelled with an aqueous-phase thickener or gelling agent and/or containing ingredients soluble in water. The water can represents from 0.01 to 50%, for example from 0.5 to 30% relative to the total weight of the composition.

Needless to say, a person skilled in the art will take care to select the optional additional additives and/or the amount thereof such that the advantageous properties of the composition according to the invention are not, or are not substantially, adversely affected by the envisaged addition.

The composition according to the invention can be in the form of a tinted or non tinted dermatological composition or a care composition for keratin materials such as the skin, the lips and/or superficial body growths, in the form of an antisun composition or body hygiene composition in particular in the form of a deodorant product or make-up-removing product in stick form. It can be used in particular as a care base for the skin, superficial body growths or the lips (lip balms, for protecting the lips against cold and/or sunlight and/or the wind, or care cream for the skin, the nails or the hair). As defined herein, a deodorant product is personal hygiene product and does not relate to care, make-up or treatment of keratin materials, including keratinous fibers.

The composition of the invention may also be in the form of a coloured make-up product for the skin, in particular a foundation, optionally having care or treating properties, a blusher, a face powder, an eye shadow, a concealer product, an eyeliner, a make-up product for the body; a make-up product for the lips such as a lipstick, optionally having care or treating properties; a make-up product for superficial body growths such as the nails or the eyelashes, in particular in the form of a mascara cake, or for the eyebrows and the hair, in particular in the form of a pencil.

Needless to say, the composition of the invention should be cosmetically or dermatologically acceptable, i.e. it should contain a non-toxic physiologically acceptable medium and should be able to be applied to the skin, superficial body growths or the lips of human beings. For the purposes of the invention, the expression "cosmetically acceptable" means a composition of pleasant appearance, odour, feel and taste.

The composition advantageously contains at least one cosmetic active agent and/or at least one dermatological active agent, i.e., an agent having a beneficial effect on the skin, lips or body growths and/or at least one coloring agent.

Coloring Agents

The coloring agent according to the invention may be chosen from the lipophilic dyes, hydrophilic dyes, pigments and nacreous pigments (i.e., nacres) usually used in cosmetic or dermatological compositions, and mixtures thereof. This coloring agent is generally present in a proportion of from 0.01% to 50% relative to the total weight of the composition, such as from 0.5% to 40% and further such as from 5% to 30%, if it is present. In the case of a composition in the form of a free or compacted powder, the amount of coloring agent in the form of solid particles that are insoluble in the medium (nacres or pigments) may be up to 90% relative to the total weight of the composition.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow or annatto. They can represent from 0.1% to 20% of the weight of the composition, for example, from 0.1% to 6% (if present). The water-soluble dyes are, for example, beetroot juice or methylene blue, and can represent up to 6% of the total weight of the composition.

The pigments may be white or coloured, mineral and/or organic, and coated or uncoated. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D & C type, and lakes based on cochineal carmine or on barium, strontium, calcium or aluminium. The pigments can represent from 0.1% to 50%, such as from 0.5% to 40% and further such as from 2% to 30% relative to the total weight of the composition, if they are present.

The nacreous pigments may be chosen from white nacreous pigments such as mica coated with titanium or with bismuth oxychloride, coloured nacreous pigments such as titanium mica with iron oxides, titanium mica with, in particular, ferric blue or chromium oxide, titanium mica with an organic pigment of the type mentioned above, as well as nacreous pigments based on bismuth oxychloride. They can represent, for example, from 0.1% to 20% relative to the total weight of the composition, and further such as from 0.1% to 15%, if they are present.

In one embodiment, the coloring agent is a pigment (nacreous or not).

Waxes

The composition can optionally contain one or more waxes to improve the structuring in stick form, although this rigid form can be obtained in the absence of wax. For the purposes of the present invention, a wax is a lipophilic fatty compound that is solid at room temperature (25° C.) and atmospheric pressure (760 mmHg, i.e. 101 KPa), which undergoes a reversible solid/liquid change of state, having a melting point of greater than 40° C. and further such as greater than 55° C. and which may be up to 200° C., and having an anisotropic crystal organization in the solid state. The size of the crystals is such that the crystals diffract and/or scatter light, giving the composition a cloudy, more or less opaque appearance. By bringing the wax to its melting point, it is possible to make it miscible with oils and to form a microscopically homogeneous mixture, but on returning the temperature of the mixture to room temperature, recrystallization of the wax in the oils of the mixture is obtained. It is this recrystallization in the mixture which is responsible for the reduction in the gloss of the mixture. Thus, the composition advantageously contains little or no wax, and in particular less than 5% wax.

For the purposes of the invention, the waxes are those generally used in cosmetics and dermatology; they are, for example, of natural origin, for instance beeswax, carnauba wax, candelilla wax, ouricury wax, Japan wax, cork fibre wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

According to the invention, the melting point values correspond to the melting peak measured by the "Differential Scanning Calorimetry" method with a temperature rise of 5 or 10° C./min.

Liposoluble or Dispersible Polymers

The composition of the invention also can contain at least one polymer that is liposoluble or dispersible in the medium, other than the structuring polymer and the at least one rheological agent, and may have film-forming properties and may have, for example, an average molecular weight of from 500 to 1 000 000, such as from 1 000 to 500 000, and for example, further such as from 5 000 to 100 000, and even further such as from 5 000 to 20 000. This at least one liposoluble polymer may contribute towards increasing the viscosity and/or improving the staying power of the film. The at least one liposoluble polymer can have a softening point of not more than 30° C.

As examples of liposoluble polymers which can be used in the invention, mention may be made of: polyalkylenes, in particular polybutene, poly(meth)acrylates, alkylcelluloses with a linear or branched, saturated or unsaturated $C_1$ to $C_8$ alkyl radical, such as ethylcellulose and propylcellulose, silicone polymers that are compatible with the fatty phase, as well as vinylpyrrolidone (VP) copolymers, and mixtures thereof.

Vinylpyrrolidone copolymers, copolymers of a $C_2$ to $C_{30}$, such as $C_3$ to $C_{22}$ alkene, and combinations thereof, can be used. As examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

Not only for the staying power properties but also for the feel and consistency properties of the film, the PVP/hexadecene copolymer having an average molecular weight of from 7 000 to 7 500 or alternatively the PVP/eicosene copolymer having an average molecular weight of from 8 000 to 9 000 can be used.

The liposoluble or dispersible polymers in the composition of the invention can be also used in an amount of from 0.01% to 20% (as active material) relative to the total weight of the composition, such as, for example, from 1% to 10%, if they are present.

Pasty Fatty Compound

The composition according to the invention also can contain at least one fatty compound that is pasty at room temperature. For the purposes of the invention, the expression "pasty fatty substances" means fatty substances with a melting point ranging from 20° C. to 55° C., such as from 25° C. to 45° C., or from 25° C. to 40° C., and/or a viscosity at 40° C. ranging from 0.1 to 40 Pa·s (1 400 poises), such as from 0.5 to 25 Pa·s, measured using a Contraves TV or Rhéomat 80 viscometer, equipped with a spindle rotating at 240 $min^{-1}$ for supplying with 60 Hz or at 200 $min^{-1}$ for supplying with 50 Hz. A person skilled in the art can select the spindle for measuring the viscosity from the spindles MS-r3 and MS-r4, on the basis of his general knowledge, so as to be able to carry out the measurement of the pasty compound tested.

According to the invention, at least one pasty fatty substance is used. The at least one pasty fatty substance can be chosen from hydrocarbon-based compounds, optionally of polymeric type; they can also be chosen from silicone compounds and/or fluoro compounds; they may also be in the form of a mixture of hydrocarbon-based compounds and/or silicone compounds and/or fluoro compounds. In the case of a mixture of different pasty fatty substances, the hydrocarbon-based pasty compounds (mainly containing hydrogen and carbon atoms and optionally ester groups) can be used in major proportion.

Among the pasty compounds which may be used in the composition according to the invention, mention may be made of lanolins and lanolin derivatives such as acetylated lanolins or oxypropylenated lanolins or isopropyl lanolate, having a viscosity of from 18 to 21 Pa·s, such as from 19 to 20.5 Pa·s, and/or a melting point of from 30° C. to 55° C. such as from 30° C. to 40° C., and mixtures thereof. It is also possible to use esters of fatty acids or of fatty alcohols, for example, those containing from 20 to 65 carbon atoms (melting point of about from 20° C. to 35° C. and/or viscosity at 40° C. ranging from 0.1 to 40 Pa·s), such as triisostearyl or cetyl citrate; arachidyl propionate; polyvinyl laurate; cholesterol esters, such as triglycerides of plant origin, such as hydrogenated plant oils, viscous polyesters such as poly(12-hydroxystearic acid), and mixtures thereof. Triglycerides of plant origin which may be used are hydrogenated castor oil derivatives, such as "Thixinr" from Rhéox.

Mention may also be made of pasty silicone fatty substances such as polydimethylsiloxanes (PDMSs) containing pendent chains of the alkyl or alkoxy type containing from 8 to 24 carbon atoms, and having a melting point of 20-55° C. and for example from 20° C. to 40° C., such as stearyldimethicones, such as, for example, those sold by the company Dow Corning under the trade names DC2503 and DC25514, and mixtures thereof.

The pasty fatty substance(s) may be present in a proportion of from 0.1% to 60% by weight, relative to the total weight of the composition, such as in a proportion of from 1% to 45% by weight, and further such as from 2 to 30% by weight, in the composition, if they are present.

The composition according to the invention may be manufactured by the known processes, that are generally used in cosmetics or dermatology. It may be manufactured by the process which comprises heating the polymer at least to its softening point, adding the gelling agent(s), the amphiphilic compound(s), the coloring agent(s) and the additive(s) thereto and then mixing everything together until a clear, transparent solution is obtained. After reducing the temperature, the volatile solvent(s) is(are) then added to the mixture obtained. The homogeneous mixture obtained can then be cast in a suitable mould such as a lipstick mould or directly into the packaging articles (case or dish in particular).

Another aspect of the invention is a lipstick composition in stick form containing at least one continuous liquid fatty phase structured with at least one non-waxy structuring polymer having a weight-average molecular mass of less than 100 000, and at least one gelling agent for theliquid fatty phase, the liquid fatty phase, the structuring polymer and the gelling agent forming a physiologically acceptable medium, the gelling agent and the structuring polymer can give the composition the appearance of a deformable elastic solid with a hardness ranging from 30 to 300 gf, such as 30 to 250 gf, and further such as 30 to 200 gf, even in the absence of wax. The hardness is measured by the "cheesewire" method described above. The non-waxy polymer may be a polymer whose skeleton comprises units containing a hetero atom, as defined previously, and further may be a polyamide that may contain (an) alkyl end group(s) linked to the skeleton via an ester group.

This lipstick composition in stick form may contain an additive chosen from fatty compounds that are pasty at room temperature, liposoluble polymers and mixtures thereof, as defined previously.

An aspect of the invention is also a care, make-up or treatment cosmetic process for keratin materials of human beings, and in particular the skin, the lips and superficial body growths, comprising the application to the keratin materials of the composition, in particular the cosmetic composition, as defined above.

An aspect of the invention is also a combination of at least one polymer having a weight-average molecular mass of less than 100 000, such as less than 50 000, comprising a) a polymer skeleton containing hydrocarbon-based repeating units containing at least one hetero atom, and b) optionally at least one pendant fatty chain and/or at least one terminal fatty chain that are optionally functionalized, containing from 8 to 120 carbon atoms and being linked to these hydrocarbon-based units, and of at least one gelling agent for the liquid fatty phase, in a cosmetic composition or for the manufacture of a physiologically acceptable composition, to obtain a solid composition, such as a wax-free composition, which does not exude and/or which can produce a glossy and/or comfortable deposit on keratin materials.

The compositions of the present invention may also further comprise water, optionally thickened with an aqueous-phase thickener or gelled with a gelling agent and/or containing ingredients soluble in water.

The invention is illustrated in greater detail in the examples which follow. The amounts are given as percentages by mass.

EXAMPLE 1

Lipstick

| Phase A | |
|---|---|
| Uniclear 100 | 18% |
| isononyl isononanoate | 5% |
| diisostearyl malate | 17% |
| hydrogenated polybutene | 4% |
| Phase B | |
| hydrophobic silica (Aerosil R972) | 3% |
| hydrogenated polybutene | 25% |
| isononyl isononanoate | 12% |
| Phase C | |
| pigments | 7% |
| hydrogenated polybutene | 9% |

Procedure

The Uniclear 100 was solubilized (or dissolved) at 100° C. in a mixture of melted oils and wax, followed by addition of the pigments and fillers. The whole mixture was mixed using a deflocculating turbomixer (Raynerie) and left stirring for 1H 30 min. The product obtained was then cast in molds for lipsticks in stick form.

a) Silica gel (phase B): The gel was prepared, with stirring in a Rayneri stirrer at 60° C., using a hotplate, by introducing the silica portionwise into the oily mixture formed from:

| | |
|---|---|
| Hydrogenated polybutene | 25 g |
| Isononyl isononanoate | 12 g |
| TOTAL | 40 g | b) Ground pigmentary material (phase C)

The pigments were mixed with the oil heated to 60° C.; the mixture was ground three times in a three-roll mill.

The sticks of lipstick obtained had a diameter of 8.1 and a hardness of 46±5 gf measured using a "cheese wire". These lipsticks were considered by testers as glossy and having good staying power. The stability of the compositions was tested using the test described herein. The composition was found to have good stability in that there was no exudation at room temperature (25° C.) or at 37° C., or at 47° C., for 2 months.

EXAMPLE 2

Lipsticks

| Phase A | |
|---|---|
| Uniclear 100 V | 18% |
| Phase B | |
| Bentone 38 V | 3% |
| diisostearyl malate | 16.3% |
| isononyl isononanoate | 2.3% |
| hydrogenated polybutene | 36.4% |
| hydrophobic silica (Aerosil R972) | 3% |
| Phase C | |
| Pigments | 7% |
| isononyl isononanoate | 14% |

The silica was placed in a heating vessel and then dispersed using a Rayneri stirrer in the mixture of oils of phase B, heated to about 60° C. When the gel obtained was homogeneous, the Bentone was added thereto. The mixture was then stirred until a homogeneous preparation was obtained, corresponding to phase B. Phase C was prepared by grinding the pigments in the hydrogenated polybutene using a three-roll mill.

Phase A was then heated to 100° C. with phase B. When the mixture obtained was homogeneous, the ground material C was added and the resulting mixture was heated for 1 h 30 min with magnetic stirring. The preparation was then cast in a mold for lipsticks in stick form.

The sticks of lipstick obtained had a diameter of 8.1 mm and a hardness of 49±5 gf. These sticks of lipstick did not exude at room temperature for several months, or at 37° C. or at 47° C. for 1 month. They deposited a glossy film which had good staying power and which did not migrate.

EXAMPLE 3

Five clear anhydrous sunscreen sticks comprising compositions of the present invention were prepared. The tables below list the ingredients used.

| TRADE NAME | RAW MATERIALS | COMPANY |
| --- | --- | --- |
| Schercemol DISM | Diisostearyl Malate | Shear Chemical Inc. |
| Ceraphyl 45 | Dioctyl Malate | ISP |
| Cristal O | Castor Oil | Chaschem |
| Nature Chem PGR | Propylene Glycol Ricinoleate | Chaschem |
| Macromelt 6212 | Polyamide Resin | Henkel Corporation |
| Parsol 1789 | Butyl Methoxydibenxoyl Methane | Givaudan-Roure |
| Neo Heliopan 303 | Octylcrylene | Haarman & Reimer |
| Ethocel | Ethyl Cellulose | Dow Chemical |

| CLEAR ANHYDROUS SUNSCREEN (With Oil Soluble Polymers) | | | | | |
| --- | --- | --- | --- | --- | --- |
| RAW MATERIALS | A | B | C | D | E |
| Schercemol DISM (oil) | 10 | 10 | 10 | 10 | 10 |
| Ceraphyl 45 (oil) | 20 | 20 | 20 | 20 | 20 |
| Cristal O (oil) | 26.15 | 24.15 | 22.9 | 23.9 | 23.15 |
| Nature Chem PGR (oil) | 10.5 | 10.5 | 10.5 | 10.5 | 10.5 |
| Macromelt 6212 (polyamide) | 16 | 16 | 16 | 16 | 16 |
| N-Hance-AG-50 (gelling) | — | 2 | — | — | — |
| N-Hance-AG-200 (gelling) | — | — | 3 | — | — |
| Ethocel 100 (gelling) | — | — | — | 2 | — |
| Ethocel 7 (gelling) | — | — | — | — | 3 |
| Cetyl Alcohol | 4 | 4 | 4 | 4 | 4 |
| Propyl Paraben | 0.1 | 0.1 | 0.1 | 0.1 | 0.1 |
| Parsol 1789 (filter) | 3 | 3 | 3 | 3 | 3 |
| Neo Heliopan 303 (filter) | 10 | 10 | 10 | 10 | 10 |
| Flavoring Oil | 0.25 | 0.25 | 0.5 | 0.5 | 0.25 |

What is claimed is:

1. A composition comprising at least one liquid fatty phase which comprises:
   (i) at least one structuring polymer comprising:
   a polymer skeleton which comprises at least one hydrocarbon-based repeating unit comprising at least one hetero atom,
   wherein said at least one structuring polymer further comprises at least one of:
   at least one terminal fatty chain chosen from alkyl chains and alkenyl chains, wherein said at least one terminal fatty chain is bonded to said polymer skeleton via at least one linking group; and
   at least one pendant fatty chain chosen from alkyl chains and alkenyl chains, wherein said at least one pendant fatty chain is bonded to said polymer skeleton via at least one linking group; and
   (ii) at least one gelling agent, with the proviso that said at least one gelling agent is not silica, methyl 12-hydroxystearate, 12-hydroxy stearic acid, or stearalkonium hectorite;
   with the proviso that said composition is not a deodorant product.

2. The composition according to claim 1, wherein the composition is anhydrous.

3. The composition according to claim 1, wherein said at least one linking group is chosen from urea, ester, and amine groups.

4. The composition according to claim 1, wherein said at least one structuring polymer has a weight-average molecular mass of less than 100,000.

5. The composition according to claim 1, wherein said at least one structuring polymer is at least one polyamide polymer comprising a polymer skeleton which comprises at least one amide repeating unit.

6. The composition according to claim 1, wherein said at least one liquid fatty phase of the composition comprises at least one polar oil and at least one apolar oil.

7. The composition according to claim 1, wherein said at least one liquid fatty phase comprises at least one non-volatile oil.

8. The composition according to claim 6, wherein said at least one fatty phase comprises at least one volatile solvent chosen from hydrocarbon-based solvents and silicone solvents optionally comprising alkyl or alkoxy groups that are pendant or at the end of the silicone chain.

9. The composition according claim 1, wherein said at least one gelling agent is chosen from gelling agents in polymeric form and gelling agents in mineral form.

10. The composition according to claim 9, wherein the at least one gelling agent is chosen from optionally modified clays, partially and totally crosslinked elastomeric polyorganosiloxanes, galactomannans comprising from 1 to 6 hydroxyl groups per saccharide, substituted with a saturated or unsaturated alkyl chain, ethylcellulose, and silicone gums and block copolymers.

11. The composition according to claim 1, wherein said at least one gelling agent is in mineral form with particle sizes that cause little or no light scattering.

12. The composition according to claim 11, wherein the at least one gelling agent is fumed silica.

13. The composition according to claim 1, wherein said at least one gelling agent is present in an amount ranging from 0.05% to 35% by weight relative to the total weight of the composition.

14. The composition according to claim 1, wherein said composition further comprises at least one amphiphilic compound that is liquid and non-volatile at room temperature and has a hydrophilic/lipophilic balance of less than 12.

15. The composition according to claim 1, wherein said composition further comprises at least one coloring agent.

16. The composition according to claim 1, wherein said composition further comprises at least one wax.

17. The composition according to claim 1, wherein said composition further comprises at least one additional additive chosen from antioxidants, essential oils, preserving agents, fragrances, fillers, waxes, fatty compounds that are pasty at room temperature, neutralizing agents, gums, liposoluble polymers and polymers that are dispersible in a lipophilic medium, cosmetic and dermatological active agents, dispersants, and an aqueous phase containing water that is optionally thickened or gelled with an aqueous-phase thickener or gelling agent and optionally water-miscible compounds.

18. A mascara, an eyeliner, a foundation, a lipstick, a blusher, a make-up-removing product, a make-up product for the body, an eyeshadow, a face powder, a concealer product, a shampoo, a conditioner, an antisun product or a care product for the skin, lips, or hair comprising a composition comprising at least one liquid fatty phase in said mascara, eyeliner, foundation, lipstick, blusher, make-up-removing product, make-up product for the body, eyeshadow, face powder, concealer product, shampoo, conditioner, antisun product or care product for the lips, face, body, or hair which comprises:
   (i) at least one structuring polymer comprising:
   a polymer skeleton which comprises at least one hydrocarbon-based repeating unit comprising at least one hetero atom, wherein said at least one structuring polymer further comprises at least one of:
  at least one terminal fatty chain chosen from alkyl chains and alkenyl chains, wherein said at least one terminal fatty chain is bonded to said polymer skeleton via at least one linking group,
  at least one pendant fatty chain chosen from alkyl chains and alkenyl chains, wherein said at least one pendant fatty chain is bonded to said polymer skeleton via at least one linking group; and
  (ii) at least one gelling agent, with the proviso that said at least one gelling agent is not silica, methyl 12-hydroxystearate, 12-hydroxy stearic acid, or stearalkonium hectorite;
  with the proviso that said composition is not a deodorant product.

19. The mascara, an eyeliner, a foundation, a lipstick, a blusher, a make-up-removing product, a make-up product for the body, an eyeshadow, a face powder, a concealer product, a shampoo, a conditioner, an antisun product or a care product for the skin, lips, or hair according to claim 18, wherein said at least one structuring polymer is chosen from polyamide polymers of formula (I):

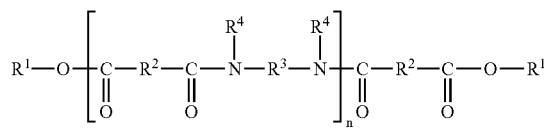

in which:
  n is an integer which represents the number of amide units such that the number of ester groups present in said at least one polyamide polymer ranges from 10% to 50% of the total number of all ester groups and all amide groups comprised in said at least one polyamide polymer;
  $R^1$, which are identical or different, are each chosen from alkyl groups comprising at least 4 carbon atoms and alkenyl groups comprising at least 4 carbon atoms;
  $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
  $R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
  $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

20. The mascara, an eyeliner, a foundation, a lipstick, a blusher, a make-up-removing product, a make-up product for the body, an eyeshadow, a face powder, a concealer product, a shampoo, a conditioner, an antisun product or a care product for the skin, lips, or hair according to claim 18, wherein said at least one structuring polymer is chosen from ethylenediamine/stearyl dimer tallate copolymer.

21. The mascara, an eyeliner, a foundation, a lipstick, a blusher, a make-up-removing product, a make-up product for the body, an eyeshadow, a face powder, a concealer product, a shampoo, a conditioner, an antisun product or a care product for the skin, lips, or hair according to claim 18, wherein said at least one structuring polymer is chosen from ethylenediamine/stearyl dimer dilinoleate copolymer.

22. The composition according to claim 1, wherein said at least one structuring polymer is chosen from polyamide polymers of formula (I):

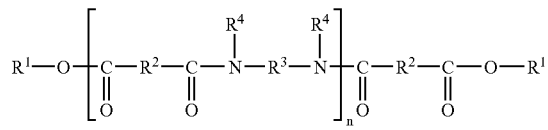

in which:
  n is an integer which represents the number of amide units such that the number of ester groups present in said at least one polyamide polymer ranges from 10% to 50% of the total number of all ester groups and all amide groups comprised in said at least one polyamide polymer;
  $R^1$, which are identical or different, are each chosen from alkyl groups comprising at least 4 carbon atoms and alkenyl groups comprising at least 4 carbon atoms;
  $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
  $R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
  $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

23. The composition according to claim 22, wherein in said formula (I), n is an integer ranging from 1 to 5.

24. The composition according to claim 22, wherein said $R^1$, which are identical or different, are chosen from $C_{12}$ to $C_{22}$ alkyl groups.

25. The composition according to claim 22, wherein said $R^2$, which are identical or different, are each chosen from $C_{10}$ to $C_{42}$ hydrocarbon based groups with the proviso that at least 50% of all $R^2$ are chosen from $C_{30}$ to $C_{42}$ hydrocarbon based groups.

26. The composition according to claim 22 wherein in said $R^3$, which can be identical or different, are each chosen from $C_2$ to $C_{36}$ hydrocarbon-based groups and polyoxyalkylene groups.

27. The composition according to claim 22, wherein in said $R^4$, which can be identical or different, are each chosen from hydrogen atoms.

28. The method composition according to claim 1, wherein said at least one structuring polymer is chosen from ethylenediamine/stearyl dimer tallate copolymer.

29. The composition according to claim 1, wherein said at least one structuring polymer is chosen from ethylenediamine/stearyl dimer dilinoleate copolymer.

30. A care and/or treatment and/or make-up composition for keratinous fibers, lips or skin comprising at least one liquid fatty phase in said care and/or treatment and/or make-up composition for keratinous fibers, lips or skin which comprises:

(i) at least one structuring polymer comprising:
a polymer skeleton which comprises at least one hydrocarbon-based repeating unit comprising at least one hetero atom, wherein said at least one structuring polymer further comprises at least one of:

at least one terminal fatty chain chosen from alkyl chains and alkenyl chains, wherein said at least one terminal fatty chain is bonded to said polymer skeleton via at least one linking group, at least one pendant fatty chain chosen from alkyl chains and alkenyl chains, wherein said at least one pendant fatty chain is bonded to said polymer skeleton via at least one linking group; and (ii) at least one gelling agent;

with the proviso that the composition is not a deodorant product.

31. A care and/or treatment and/or make-up composition according to claim 30, wherein said at least one structuring polymer is chosen from ethylenediamine/stearyl dimer tallate copolymer.

32. A care and/or treatment and/or make-up composition according to claim 30, wherein said at least one structuring polymer is chosen from ethylenediamine/stearyl dimer dilinoleate copolymer.

33. A method for care, make-up or treatment of keratin materials comprising applying to said keratin materials a composition comprising at least one liquid fatty phase which comprises:

(i) at least one structuring polymer comprising:
a polymer skeleton which comprises at least one hydrocarbon-based repeating unit comprising at least one hetero atom, wherein said at least one structuring polymer further comprises at least one of:

at least one terminal fatty chain chosen from alkyl chains and alkenyl chains, wherein said at least one terminal fatty chain is bonded to said polymer skeleton via at least one linking group, at least one pendant fatty chain chosen from alkyl chains and alkenyl chains, wherein said at least one pendant fatty chain is bonded to said polymer skeleton via at least one linking group; and (ii) at least one gelling agent;

with the proviso that the composition is not a deodorant product.

34. The method according to claim 33, wherein said at least one structuring polymer is chosen from ethylenediamine/stearyl dimer tallate copolymer.

35. The method according to claim 33, wherein said at least one structuring polymer is chosen from ethylenediamine/stearyl dimer dilinoleate copolymer.

* * * * *

UNITED STATES PATENT AND TRADEMARK OFFICE
CERTIFICATE OF CORRECTION

| | |
|---|---|
| PATENT NO. | : 7,314,612 B2 |
| APPLICATION NO. | : 10/203254 |
| DATED | : January 1, 2008 |
| INVENTOR(S) | : Ferrari et al. |

It is certified that error appears in the above-identified patent and that said Letters Patent is hereby corrected as shown below:

In claim 28 at col. 32, line 65, the phrase "The method composition according to claim 1," should read -- The composition according to claim 1,--.

Signed and Sealed this

Sixth Day of May, 2008

JON W. DUDAS
*Director of the United States Patent and Trademark Office*